US012127895B2

United States Patent
Vargas et al.

(10) Patent No.: US 12,127,895 B2
(45) Date of Patent: Oct. 29, 2024

(54) ATTACHMENT MECHANISM FOR DOCKING CANNULAS TO SURGICAL ROBOTIC ARMS

(71) Applicant: Verb Surgical Inc., Santa Clara, CA (US)

(72) Inventors: Matthew Vargas, San Francisco, CA (US); Alec Gordon, Berkeley, CA (US); Nathan Wang, Austin, TX (US); Andrea Bajo, Palo Alto, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/467,602

(22) Filed: Sep. 14, 2023

(65) Prior Publication Data

US 2024/0000539 A1    Jan. 4, 2024

Related U.S. Application Data

(62) Division of application No. 17/039,979, filed on Sep. 30, 2020, now Pat. No. 11,793,597.

(51) Int. Cl.
*A61M 25/00*    (2006.01)
*A61B 17/34*    (2006.01)
(Continued)

(52) U.S. Cl.
CPC .......... *A61B 90/57* (2016.02); *A61B 17/3415* (2013.01); *A61B 34/25* (2016.02);
(Continued)

(58) Field of Classification Search
CPC ..... A61B 90/57; A61B 17/3415; A61B 34/25; A61B 34/35; A61B 34/37; A61B 34/70;
(Continued)

(56) References Cited

U.S. PATENT DOCUMENTS 5,807,378 A    9/1998 Jensen et al.
6,451,027 B1 *  9/2002 Cooper .............. A61B 1/00149
                                                901/19

(Continued)

FOREIGN PATENT DOCUMENTS

CN    106102642 A    11/2016
JP    2012-254360 A    12/2012
(Continued)

OTHER PUBLICATIONS

An Improved 6-D Pose Detection Method Based on Opposing-Magnet Pair System and Constraint Multiple Magnets Tracking Algorithm; IEEE Sensors Journal, vol. 17, No. 20, Oct. 15, 2017, by Shuang Song, Xiaoxiao Qiu, Wei Liu, and Max Q.-H. Meng; 2017: 8 pages.

(Continued)

*Primary Examiner* — Amy J. Sterling
(74) *Attorney, Agent, or Firm* — Aikin & Gallant, LLP

(57) ABSTRACT

A cannula sterile adapter for attachment of a cannula to a robotic surgical system, the adapter comprising: a rigid barrier portion having a cannula interface defining an opening dimensioned to receive a cannula lug, a first cannula interface structure extending from the cannula interface, and a second cannula interface structure, the first cannula interface structure and the second cannula interface structure are dimensioned to interface with alignment structures of a cannula lug; and a flexible barrier portion molded to the rigid barrier portion, the flexible barrier portion defining a cavity around the opening of the rigid barrier portion that is dimensioned to receive a cannula lug inserted therein, the cavity having a first side defined by the first cannula interface structure and a second side along which the second cannula interface structure is positioned, and wherein the (Continued)

second cannula interface structure is entirely surrounded by the flexible barrier portion.

20 Claims, 21 Drawing Sheets

(51) Int. Cl.
 *A61B 34/00*  (2016.01)
 *A61B 34/35*  (2016.01)
 *A61B 34/37*  (2016.01)
 *A61B 90/57*  (2016.01)
 *A61B 34/30*  (2016.01)

(52) U.S. Cl.
 CPC .............. *A61B 34/35* (2016.02); *A61B 34/37* (2016.02); *A61B 34/70* (2016.02); *A61B 2034/301* (2016.02); *A61B 2090/571* (2016.02)

(58) Field of Classification Search
 CPC ........ A61B 2034/301; A61B 2090/571; A61B 90/06; A61B 2090/067; A61B 34/74; A61B 2017/00477; A61B 2562/0219; A61B 2562/0223; A61B 34/30
 See application file for complete search history.

(56) References Cited

U.S. PATENT DOCUMENTS

| | | | |
|---|---|---|---|
| 7,314,331 | B1 | 1/2008 | Koros et al. |
| 8,182,469 | B2 | 5/2012 | Anderson et al. |
| 8,512,312 | B2* | 8/2013 | Sage .................. A61M 39/1011 604/513 |
| 11,076,883 | B2 | 8/2021 | Scheib |
| 11,090,122 | B2 | 8/2021 | Fuerst et al. |
| 11,911,585 | B2* | 2/2024 | Hall ....................... A61M 39/12 |
| 2006/0161136 | A1 | 7/2006 | Anderson et al. |
| 2008/0033462 | A1* | 2/2008 | Di Nardo ................ A61F 9/007 606/166 |
| 2008/0147089 | A1 | 6/2008 | Loh et al. |
| 2008/0208202 | A1 | 8/2008 | Williams |
| 2009/0043246 | A1 | 2/2009 | Dominguez |
| 2011/0071359 | A1* | 3/2011 | Bonadio ............ A61B 17/0293 600/184 |
| 2011/0105954 | A1 | 5/2011 | Cohen et al. |
| 2011/0282351 | A1 | 11/2011 | Cooper et al. |
| 2012/0209291 | A1 | 8/2012 | Anderson et al. |
| 2013/0298715 | A1 | 11/2013 | Valdastri et al. |
| 2014/0275955 | A1 | 9/2014 | Crawford et al. |
| 2015/0133958 | A1 | 5/2015 | Singh et al. |
| 2016/0242861 | A1 | 8/2016 | Flatt et al. |
| 2017/0086930 | A1 | 3/2017 | Thompson et al. |
| 2017/0105811 | A1 | 4/2017 | Garbus et al. |
| 2018/0008313 | A1* | 1/2018 | Augelli .............. A61B 17/3417 |
| 2018/0049824 | A1 | 2/2018 | Harris et al. |
| 2018/0055577 | A1 | 3/2018 | Barral et al. |
| 2018/0168746 | A1 | 6/2018 | Swayze et al. |
| 2018/0283842 | A1 | 10/2018 | Rueb et al. |
| 2018/0289431 | A1 | 10/2018 | Draper et al. |
| 2019/0053824 | A1 | 2/2019 | Scheib |
| 2019/0201120 | A1 | 7/2019 | Shelton et al. |
| 2019/0231458 | A1* | 8/2019 | DiMaio ................ A61B 34/30 |
| 2019/0231461 | A1* | 8/2019 | Steger .................... A61B 34/30 |
| 2019/0321115 | A1 | 10/2019 | Anderson et al. |
| 2020/0138534 | A1 | 5/2020 | Garcia et al. |
| 2020/0268453 | A1 | 8/2020 | Fuerst et al. |
| 2020/0397477 | A1* | 12/2020 | Schaller ................. A61F 9/007 |
| 2021/0128260 | A1 | 5/2021 | Gonenc et al. |
| 2021/0290311 | A1 | 9/2021 | Fuerst et al. |
| 2021/0330351 | A1 | 10/2021 | Scheib |
| 2021/0353369 | A1 | 11/2021 | Fuerst et al. |

FOREIGN PATENT DOCUMENTS

| | | |
|---|---|---|
| JP | 2017-513552 A | 6/2017 |
| JP | 2019-524284 A | 9/2019 |
| KR | 10-2014-0020071 A | 2/2014 |
| WO | 2010/104753 A1 | 9/2010 |
| WO | 2014/011539 A2 | 1/2014 |
| WO | 2015/142785 A1 | 9/2015 |
| WO | 2019/096939 A1 | 5/2019 |
| WO | 2019/204699 A1 | 10/2019 |

OTHER PUBLICATIONS

Gmerek, Artur, et al., "Admittance control of a 1-DoF robotic arm actuated by BLDC motor", 17th International Conference on Methods & Models in Automation & Robotics (MMAR), Aug. 27, 2012, 6 pages.
He, Changyu, et al., "An Inertial and Optical Sensor Fusion Approach for Six Degree-of-Freedom Pose Estimation", Sensors, vol. 15, Jul. 8, 2015, pp. 16448-16465.
International Preliminary Report on Patentability received for PCT Patent Application No. PCT/IB21/058696, mailed on Apr. 13, 2023, 6 pages.
International Search Report and Written Opinion for International Application No. PCT/IB2021/058696 mailed Feb. 15, 2022, 15 pages.
Non-Final Office Action received for U.S. Appl. No. 17/039,979, mailed on Apr. 18, 2023, 8 pages.
Notice of Allowance received for U.S. Appl. No. 17/039,979, mailed on Aug. 15, 2023, 7 pages.
Notice of Allowance received for U.S. Appl. No. 17/039,979, mailed on Aug. 31, 2023, 2 pages.
Notice of Allowance received for U.S. Appl. No. 17/039,981, mailed on Aug. 2, 2023, 2 pages.
Notice of Allowance received for U.S. Appl. No. 17/039,981, mailed on Jun. 30, 2023, 10 pages.
Requirement for Restriction/Election received for U.S. Appl. No. 17/039,979, mailed on Feb. 6, 2023, 6 pages.
Steidle, Florian, et al., "Optical-Inertial Tracking of an Input Device for Real-Time Robot Control," 2016 IEEE International Conference on Robotics and Automations (ICRA), May 16, 2016, pp. 742-749.
Tracking Position and Orientation of Magnetic Objects Using Manetometer, by Niklas Wahlstrom and Fredrik Gustafsson; Linkoping University Post Print <http://um.kb.se/resolve?urn=um:nbn:se:liu:diva-122395> 14 pages; 2015.
Non-Final Office Action received for U.S. Appl. No. 17/039,977, mailed on Jul. 1, 2024, 9 pages.

* cited by examiner

ATTACHMENT MECHANISM FOR DOCKING CANNULAS TO SURGICAL ROBOTIC ARMS

CROSS-REFERENCE TO RELATED APPLICATIONS

This application is a divisional of U.S. patent application Ser. No. 17/039,979, filed Sep. 30, 2020, entitled "ATTACHMENT MECHANISM FOR DOCKING CANNULAS TO SURGICAL ROBOTIC ARMS," which is hereby incorporated by reference in its entirety.

TECHNICAL FIELD

This disclosure relates generally to the field of robotic surgery and, more particularly, to systems and methods for surgical arm docking.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

During a robotic MIS, a surgeon or other operator may use a number of different surgical instruments to perform a procedure at a surgical site. Oftentimes, a surgeon may rely on the use of a trocar or a cannula to target a site within a patient's body. The cannula may provide a channel or opening through which additional surgical instruments may be introduced and removed by a surgeon. For example, a cannula can be positioned within a patient in a body cavity, and a surgical instrument can be inserted into the cannula and guided to the body cavity via the cannula. In a robotic system, the cannula may be mounted to one or more robotic arms, which may be remotely controlled by the surgeon to move the cannula. A cannula mount may be used to attach the cannula to a robotic arm to ensure proper control and placement of the cannula within the patient.

SUMMARY

In MIS procedures, once a cannula of a trocar is properly positioned and inserted through tissue and into an interior region of a patient, a robotic arm, or a tool drive, is attached to the cannula to provide a rigid mechanical attachment of the robotic arm and the cannula. Such attachment of the robotic arm and the cannula can, for example, provide stabilization of the cannula such that one or more surgical tools can be inserted through a lumen of the cannula and into the interior region of the patient. In this regard, an attachment device or docking interface located on a distal block of the robotic arm/tool drive is maneuvered until the attachment device is aligned with an attachment portion (e.g., a cannula lug) of the cannula exposed outside the patient. The attachment device or interface of the robotic arm/tool drive is then latched (or clamped) to the attachment portion of the cannula to provide the rigid mechanical attachment of the robotic arm/tool drive and the cannula.

The robotic arm (on a surgical table or on a cart) may be manually or autonomously guided toward the cannula within the surgical port (incision) by the surgical staff or the surgeon. The goal is to "dock" the surgical arm to the cannula/trocar to establish a rigid connection and then deploy surgical tools through the access channel. Because of the delicate nature of interacting with surgical incision and the confined space in the operating room, this operation should be carried out by one person with one hand on the robot and one hand on the cannula. The user's ability to grab the arm, however, is limited by the cannula latch (e.g., lever or actuator of the attachment device) position and the arm geometry. For example, the latch might not be accessible in all configurations and the geometry of the arm might provide pinch points. In one aspect, an improved way of docking an arm is provided which maintains a mechanical connection, allowing the user to grab the arm anywhere he/she wants, and provides audible, tactile, and visual feedback on the success of the task. Representatively, a docking interface or attachment device is provided that automatically steps through the three required states during arm to cannula docking. The states are: 1) lock-out open position that allows the user to signal to the system that "docking mode" is in process, 2) mechanical detection that a cannula latch is in the correct position for docking, 3) automatic clamping of the cannula latch and signaling to the user. Representatively, the attachment device may include a lever or actuator coupled to the clamp that has a lock-out mechanism that, when triggered by the user, keeps the clamp in the open configuration (open position). This configuration is maintained until a cannula is "mechanically" detected and the mechanisms automatically steps through the clamping action.

In another aspect, the system may include sensing and logic for detecting the docking of the cannula to the surgical robotic arms using the attachment device. Representatively, a group of sensors may be integrated into the attachment device or interface that drive a finite state machine to detect presence of the cannula, proper latching or clamping onto the cannula, the type of cannula that has been docked, and any scenarios that could indicate cannula release. Each of these states can then be communicated to the user using visual, audio, or other forms of feedback on the robotic arm, as well as via any form of similar feedback on the surgeon bridge. Representatively, when the robotic arm is ready to be docked to a cannula, the latch, lever or actuator may be pressed to open the attachment device and allow it to sit on the lockout that holds the latch open. This movement of the latch actuator may be sensed by two, redundant latch position encoders and enable a gravity compensated active back (GCAB) driving mechanism associated with the surgical robotic arm for positioning of the arm to the docking position. Once the arm is positioned and the cannula is pushed into the distal block, the lockout will be disengaged allowing the latch to close and secure the cannula to the arm. At this point the latch position encoders may sense that the attachment device has been closed and has passed a mechanical over-center point, which deactivates GCAB and holds the arm in that docked position. The signal from these encoders is actively monitored and if the lever or latch is accidentally depressed after a cannula has been docked, the state machine will transition to an error state that should stop the procedure and notify the user.

In another aspect, the invention provides an over center latching mechanism, structural alignment features as part of the attachment device and/or cannula to ensure proper attachment between the attachment device and the cannula and/or a cannula sterile adapter having both flexible and rigid portions to ensure proper attachment and/or alignment between the cannula and attachment device. Representatively, the attachment device may include a lever, actuator or the like with an over center configuration that ensures that the lever (or latch) cannot be back driven to an open position by forces applied to the cannula. Once over center, the latch will increasingly force itself closed with any increasing load applied to the cannula. This aspect ensures that the cannula is held securely and reliably to the robotic arm during surgery. In another aspect, the cannula and attachment device interfaces may have alignment features that mate with one another to ensure proper alignment and attachment of the cannula to the attachment device. In still further aspects, the sterile adapter that sits between the cannula and the attachment device may have both rigid and structural features that allow the interfacing surfaces of the cannula and attachment device alignment features to mate with one another and provide for a secure attachment between the two structures.

In another aspect, the attachment device may include a ball bearing trigger mechanism that reduces wear and increases reliability of the attachment device. Representatively, the lock out mechanism of the attachment device (which holds the device in the open configuration) may include a trigger hook that interfaces with a ball bearing on the lever or actuator, instead of a fixed structure. This, in turn, reduces wear between the interfacing surfaces. In addition, the geometry of the trigger hook may be configured to have a particular size and shape that allows a desired amount of force to transition the lock out mechanism between the lock out open position in which it engages the bearing and the closed position in which the hook disengages the bearing.

In another aspect, the attachment device may have an adjustment mechanism for adjusting the docking force required to transition the attachment device between the lock out open position (e.g., the lock out mechanism is engaged with the ball bearing) and closed positions (e.g., the lock out mechanism disengages the ball bearing). For example, the attachment device may include a set screw positioned between the lock out mechanism hook and the bearing that biases the lockout towards disengagement when tightened. As the lockout adjustment set screw is tightened, it presses against the bearing and shifts the lockout such that it has less engagement with the lockout bearing than before it was tightened. By shortening the distance that the lockout has to travel to become disengaged, the force is able to be lowered. The opposite can be achieved by loosening the adjustment screw and allowing more engagement. In some aspects, the adjustment mechanism is operable to adjust the force required to disengage the lock out bearing to within a range of from 3 pounds of force to 14 pounds of force.

Representatively, on one aspect, an apparatus for attaching a cannula to a robotic surgical system includes a first clamp component configured to transition between an open position and a closed position; a second clamp component spaced from the first clamp component, the first and second clamp components defining a region configured to receive a portion of the cannula and configured to retain the portion of the cannula in the region when the first clamp component is in the closed position; and a locking component configured to lock the first clamp component in the open position and allow the first clamp component to automatically transition to the closed position based on a position of the portion of the cannula within the region. In one aspect, the locking component locks the first component in the open position when the position of the portion of the cannula is misaligned within the region. In another aspect, the first clamp component automatically transitions from the open position to the closed position when the position of the portion of the cannula is aligned within the region. In another aspect, the cannula contacts a portion of the locking component when it is aligned within the region and causes the locking component to disengage with the first clamp component allowing the first clamp component to transition from the open position to the closed position. Still further, the locking component may mechanically detect whether the portion of the cannula is in an aligned or misaligned position within the region. The apparatus may further include one or more processors configured to signal to the robotic surgical system that a user is in the process of attaching the cannula to the robotic surgical system when the first clamp component is in the open position and the portion of the cannula is within the region.

In another aspect, a system for attaching a cannula to a robotic surgical system, the system includes a clamp assembly having an open position configured to receive a cannula, and a closed position configured to attach the cannula to a robotic arm of the robotic surgical system; a lock assembly coupled to the clamp assembly, the lock assembly configured to lock the clamp assembly in the open position and allow the clamp assembly to automatically transition to the closed position based on a position of the cannula within the clamp assembly; and one or more processors configured to signal to the robotic surgical system that the clamp assembly is in a docking mode when the clamp assembly is locked in the open position or a clamping mode when the clamp assembly is locked in the closed position. In some aspect, in the docking mode, the clamp assembly remains locked in the open position until the detected position of the cannula is a position suitable for attachment to the surgical robotic system. In the clamping mode, the surgical robotic system may notify a user that the cannula is attached to the robotic surgical system. In another aspect, the lock assembly may lock the clamp assembly in the open position when the detected position of the cannula is misaligned. In some aspects, the lock assembly is further configured to transition the clamp assembly from the open position to the closed position when the detected position of the cannula is aligned. The lock assembly may include a lever coupled to a lock out mechanism that locks or unlocks the clamping assembly based on the position of the cannula.

In another aspect, a system for detecting an attachment of a cannula to a robotic surgical system may include a clamp assembly having an open position configured to receive a cannula, and a closed position configured to attach the cannula to a robotic arm of the robotic surgical system; a sensor assembly operable to sense a characteristic of the clamp assembly; and one or more processors configured to determine a state of the clamp assembly based on the characteristic sensed by the one or more sensors, and provide feedback to the user relating to the state of the clamp assembly. The clamp assembly may include a lever that is operable to transition the clamp assembly between the open position and the closed position, and the sensor assembly comprises a position sensor coupled to the lever. In some aspects, the characteristic sensed by the position sensor is an angle of the lever. In some aspects, the state of the clamp assembly determined by the one or more processors is the open position or the closed position, and is determined based on the angle of the lever. In some aspects, a visual feedback mechanism or an audio feedback mechanism that indicates to the user the state of the clamp assembly is (1) the cannula is present within the clamp assembly or (2) the cannula has been released from the clamp assembly may be provided.

In another aspect, a system for detecting an attachment of a cannula to a robotic surgical system includes a clamp assembly having an open position configured to receive a cannula, and a closed position configured to attach the cannula to a robotic arm of the robotic surgical system; a sensor assembly operable to sense a characteristic the cannula when received by the clamp assembly; and one or more processors configured to determine a state of the cannula based on the characteristic sensed by the one or more sensors, and provide feedback to the user relating to the state of the cannula. In some aspects, the position sensor is a magnetic encoder and the cannula comprises a magnet that is sensed by the magnetic encoder to sense the characteristic if the cannula. In another aspect, the characteristic of the cannula comprises a presence of the cannula within a receiving portion of the clamp assembly. In some aspects, the state of the cannula determined based on the characteristic is that the cannula is properly attached to the robotic arm or that the cannula attachment to the robotic arm is released. In another aspect, the characteristic of the cannula is a type of cannula within the receiving portion of the clamp assembly. In some aspects, the type of cannula within the receiving portion of the clamp assembly is determined based on an angle of the magnet coupled to the cannula. In another aspect, the system includes a visual feedback mechanism or an audio feedback mechanism.

In another aspect, a method for controlling an attachment of a cannula to a robotic surgical system may include a clamp assembly configured to attach a cannula to a robotic surgical system, the clamp assembly operable to transition between an open position configured to receive the cannula and a closed position to attach the cannula to the robotic surgical system; a sensor assembly operable to detect whether the clamp assembly is in the open position or the closed position, or a presence of the cannula received by the clamp assembly; and one or more processors configured to control an attachment of the cannula to the robotic surgical system based on the detection by the sensor assembly. In some aspects, when the sensor assembly detects the clamp assembly is in the open position, the one or more processors cause the surgical robotic system to disengage a braking assembly associated with a surgical robotic arm coupled to the clamping assembly; engage a gravity compensated active back driving mechanism associated with the surgical robotic arm to allow for positioning of the cannula within the clamping assembly. In another aspect, when the sensor assembly detects a transition of the clamp assembly to the closed position, the one or more processors cause the surgical robotic system to engage a braking assembly associated with a surgical robotic arm; and disengage the gravity compensated active back driving mechanism associated with the surgical robotic arm so that a current position of the cannula relative to the clamping assembly is maintained. In another aspect, when the sensor assembly detects a transition of the clamp assembly to the closed position, the one or more processors cause the surgical robotic system to engage a braking assembly associated with a surgical robotic arm coupled to the cannula; and disengage the gravity compensated active back driving mechanism associated with the surgical robotic arm. In another aspect, the sensor assembly further detects the cannula is present within the clamp assembly, and upon detecting the cannula is present, the one or more processors cause the surgical robotic system to notify a user that the cannula is attached to the surgical robotic system. In another aspect, the sensor assembly further detects the cannula is present within the clamp assembly, and upon detecting the cannula is present, the one or more processors cause the surgical robotic system to determine a type of cannula; and notify a user of the type of cannula. In another aspect, when the sensor assembly detects a transition of the clamp assembly to the open position, detects the cannula is not present within the clamp assembly, or does not sense a cannula identifier (ID) the one or more processors cause the surgical robotic system to engage a braking assembly associated with a surgical robotic arm; and notify a user that the surgical robotic system is ready for cannula attachment.

In another aspect, an apparatus for attachment of a cannula to a robotic surgical system may include a clamp operable to transition between an open position configured to receive a cannula and a closed position to attach the cannula to a robotic surgical system; an actuator operable to transition the clamp between the open position and the closed position; and a linking member pivotally coupled to the camp at a first pivot point and the actuator at a second pivot point, and wherein in the closed position, the second pivot point is over center relative to the first pivot point. In some aspects, in the closed position, the second pivot point is over center relative to the first pivot point by an angle of one degree or less. In another aspect, having the second pivot point over center relative to the first pivot point causes the clamp to increasingly force itself to the closed position with any increasing load applied to the cannula attached to the robotic surgical system. In another aspect, having the second pivot point over center relative to the first pivot point prevents the clamp from transitioning to the open position when a force is applied to the cannula attached to the robotic surgical system. In another aspect, the clamp may include a first end rotatably coupled to a base member at a third pivot point and a second end that rotates to a forward position to attach the cannula to the robotic surgical system. The second end may include a cannula mating feature configured to reinforce the attachment of the cannula to the robotic surgical system. In some aspects, the actuator is coupled to the base member at a fourth pivot point to form a four bar linkage mechanism. In some aspects, the actuator comprises a first end configured to allow a user to manually cause the actuator to transition the clamp to the open position and a second end proximate to a lockout mechanism, wherein the lock out mechanism engages with the actuator to lock the clamp in the open position, and disengages with the actuator to allow the clamp to transition to the closed position upon being contacted by the cannula. In another aspect, the apparatus may further include a base member having a cannula receiving chamber within which the cannula is positioned when attached to the robotic surgical system by the clamp, and wherein the receiving chamber comprises a cannula mating feature to guide the cannula into the receiving chamber and prevent misalignment of the cannula.

In another aspect, a sterile adapter for attachment of a cannula to a robotic surgical system includes a rigid barrier portion having a cannula interface defining an opening dimensioned to receive a cannula lug, a first cannula interface structure extending from the cannula interface, and a second cannula interface, the first cannula interface and the second cannula interface are dimensioned to interface with alignment structures of a cannula lug; and a flexible barrier portion molded to the rigid barrier portion, the flexible barrier portion defining a cavity around the opening of the rigid barrier portion that is dimensioned to receive a cannula lug inserted therein, the cavity having a first side defined by the first cannula interface structure and a second side along which the second cannula interface structure is position, and wherein the second cannula interface structure is entirely surrounded by the flexible barrier portion. In some aspects, the cannula interface includes a plate having an arm side that faces a robotic surgical arm of the robotic surgical system and a cannula side that faces the cannula lug, and the first cannula interface structure extends from the arm side in a direction of the robotic surgical arm. The flexible barrier portion may be molded to the arm side of the plate and defines at least three sides of the cavity. In some aspects, the first cannula interface structure may include a keel shaped structure dimensioned to interface with a complimentary recessed region of the cannula lug. In some aspects, the rigid clamp interface portion may include a plate molded to the second side. In some aspects, an angle of the plate is modifiable to an angle of the alignment structures of the cannula lug. In some aspects, a retention bump is coupled to the second side of the flexible barrier portion, and the retention bump dimensioned to retain the cannula sterile adapter within a clamping assembly during insertion and removal of the cannula lug within the clamping assembly. In addition, a mating datum may be coupled to a third side of the flexible barrier portion and configured to maintain an alignment between the cannula lug inserted therein and an axis of an associated tool. In some aspects, the rigid barrier portion is formed by a plastic material. In some aspects, the flexible barrier portion is formed by a flexible elastomeric material that is overmolded to the rigid barrier portion. In some aspects, the flexible barrier portion includes a thermoplastic polyurethane.

In another aspect, an apparatus for attaching a cannula to a robotic surgical system may include a clamp assembly configured to attach a cannula to a robotic surgical system, the clamp assembly comprising an actuator coupled to a clamp to transition the clamp between an open position configured to receive the cannula and a closed position to attach the cannula to the robotic surgical system; and a lock out assembly coupled to the clamp assembly to control the transition of the clamp, the lock out assembly having a hook that is dimensioned to engage a bearing coupled to the actuator when the clamp is in the open position and disengage the bearing to allow the clamp to automatically transition to the closed position. In some aspects, the hook may include a tip that extends beyond a tangent point of the bearing to engage the bearing, and when the tip is aligned with the tangent point, the hook disengages the bearing to allow the clamp to transition to the closed position. In some aspects, aligning the tip with the tangent point causes a rotation of the bearing that allows the hook to disengage the bearing. In some aspects, the hook is coupled to a spring to bias the hook to engage the bearing. In some aspects, the engagement or disengagement between the hook and the bearing provides an audible feedback or haptic feedback that notifies the user of an engagement state of the lock out assembly. The lock out assembly may be disengaged from the bearing when contacted by a cannula inserted into the clamp assembly. The apparatus may further include an adjustment mechanism operable to adjust a force required to cause the hook to engage or disengage the bearing. The adjustment mechanism may include a set screw that is adjustable between a first position that increases a spacing between the hook and the bearing and a second position that decreases the spacing between the hook and the bearing. In some aspects, in the first position, a force required to cause the hook to disengage the bearing is reduced. In some aspects, in the second position, a force required to cause the hook to disengage the bearing is increased.

In another aspect, an apparatus for attaching a cannula to a robotic surgical system may include a clamp operable to transition between an open position configured to receive the cannula and a closed position to attach the cannula to the robotic surgical system; a locking assembly coupled to the clamp assembly to hold the clamp in the open position and release the clamp to the closed position upon application of a force by a cannula, the locking assembly having a lock out hook that engages a lock out bearing of the clamp in the open position and disengages the lock out bearing to release the clamp to the closed position; and an adjustment member operable to adjust a force required to disengage the lock out bearing. In some aspects, the lock out hook is biased toward engagement of the lock out bearing by a spring. In another aspect, the adjustment member shifts a position of the lock out hook away from the lock out bearing to reduce the force required to disengage the lock out bearing. In another aspect, the adjustment member shifts a position of the lock out hook toward the lock out bearing to increase the force required to disengage the lock out bearing. In some aspects, the adjustment member includes a set screw extending through the lock out hook to an interface between the lock out hook and the lock out bearing. In one aspect, tightening the set screw shifts the position of the lock out hook away from the lock out bearing. In another aspect, loosening the set screw shifts the position of the lock out hook toward the lock out bearing. In some aspects, the lock out bearing is a ball bearing. In another aspect, the clamp may include an actuator that is coupled to a first clamp component of the clamp and is operable to move the first clamp component between the open position and the closed position, and the ball bearing is coupled to the actuator.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 1:
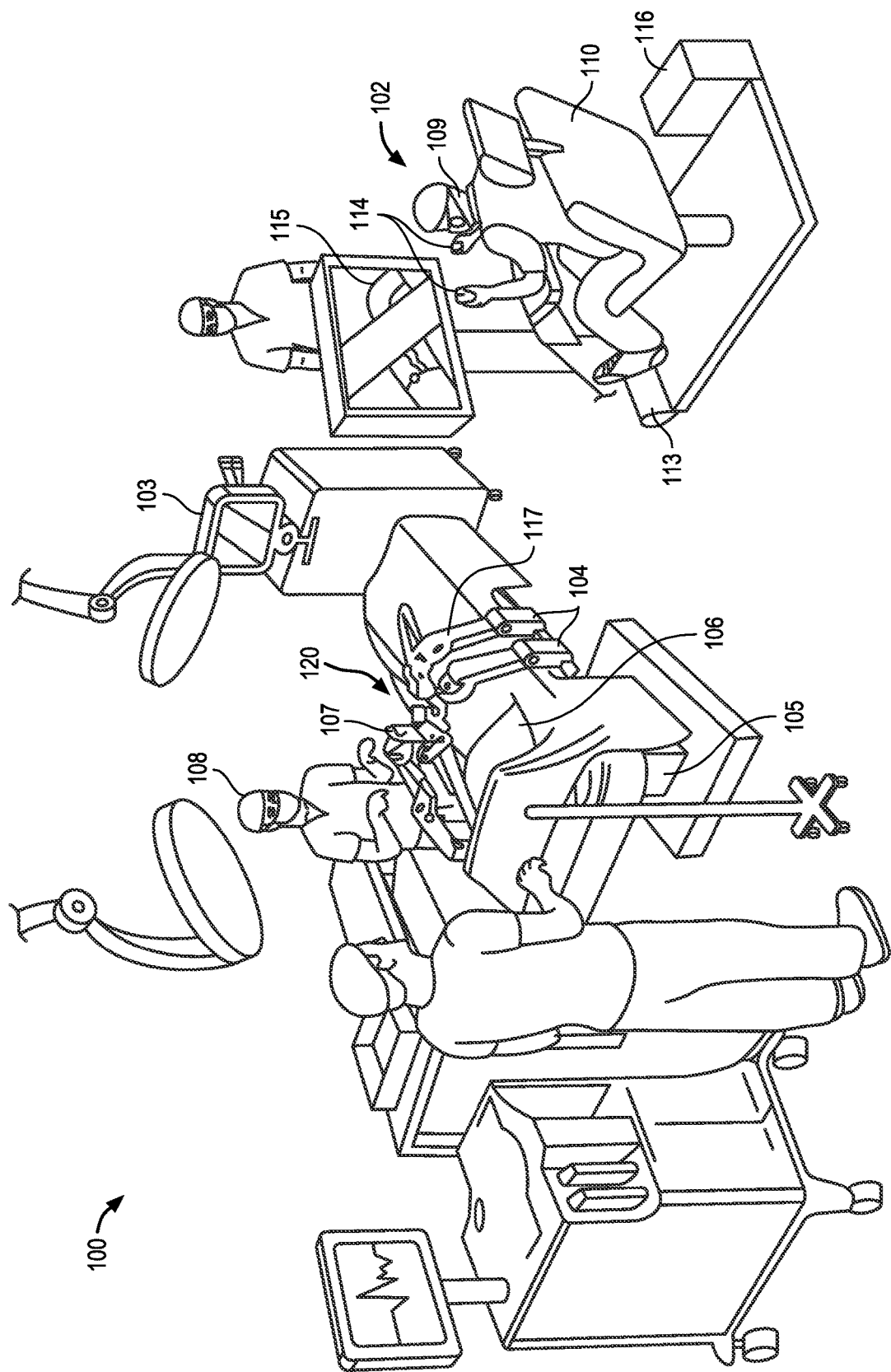
FIG. 1 is an overview schematic of an operating room arrangement with a surgical robotic system.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. Teleoperation may be engaged or disengaged based on the user actions. It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that a detected movement is an unintended action or movement by the user or the user engages in any other action which suggests teleoperation mode should no longer be engaged.

The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site). To create a port for enabling introduction of a surgical instrument into the patient 106, a trocar assembly may be at least partially inserted into the patient through an incision or entry point in the patient (e.g., in the abdominal wall). The trocar assembly may include a cannula or trocar, an obturator, and/or a seal. In some variations, the trocar assembly can include an obturator such as a needle with a sharpened tip for penetrating through a patient's skin. The obturator may be disposed within the lumen of the cannula when being inserted into the patient 106, and then removed from the cannula such that a surgical instrument may be inserted through the lumen of the cannula. Once positioned within the body of the patient 106, the cannula may provide a channel for accessing a body cavity or other site within the patient 106, for example, such that one or more surgical instruments or tools can be inserted into a body cavity of the patient 106, as described further herein. It will be understood that the cannula as described herein may be part of a trocar, and can optionally include an obturator or other components.

Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. When the user is finished controlling the surgical tools with the UIDs 114, the user may dock (i.e., store) the UIDs 114 with docking stations or UID holders located on the console 102. For example, the console 102 may include docking stations 130 at each of the left and right arm rests of the chair 110. To dock the UIDs 114, the user may move the left UID 114 to the left docking station 130 and the right UID 114 to the right docking station 130, and place each UID in their respective docking station holder.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

Figure 2:
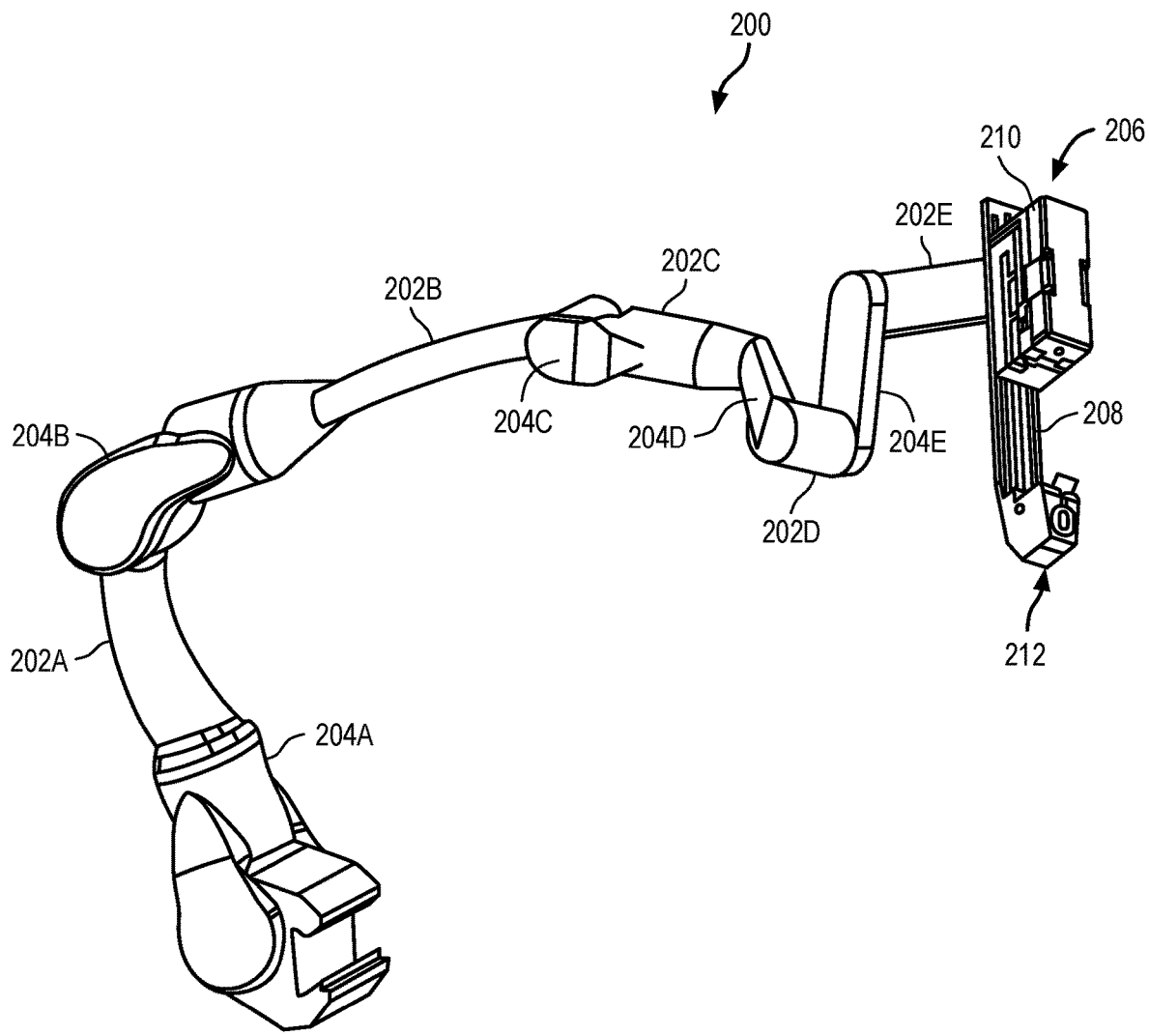
FIG. 2 is a perspective view of a portion of a robotic arm according to one aspect of the disclosure.

Turning to FIG. 2, a portion of a robotic arm 200 (e.g., robotic arm 104) is illustrated according to one aspect of the disclosure. The robotic arm 200 and associated components described herein can form a surgical robotic system according to an embodiment of the disclosure. The robotic arm 200 can be incorporated into the surgical robotic system 100 described in reference to FIG. 1, or can form a portion of a different system. While a single robotic arm 200 is illustrated, it will be understood that the robotic arm 200 may include additional arm portions or may be a component of a multi-arm apparatus without departing from the disclosure.

The robotic arm 200 may include a plurality of links (e.g., links 202A-202E) and a plurality of joint modules (e.g., joints 204A-204E) for actuating the plurality of links relative to one another. The joint modules can include various joint types, such as a pitch joint or a roll joint, any of which can be actuated manually or by the robotic arm actuators (e.g., actuators 117), and any of which may substantially constrain the movement of the adjacent links around certain axes relative to others. As also shown, a tool drive 206 is attached to the distal end of the robotic arm 200. As described herein, the tool drive 206 can be configured with an attachment device or docking interface 212 to receive an attachment portion (e.g., a mating interface or cannula lug) of a cannula and attach the cannula to the robotic arm such that one or more surgical instruments (e.g., endoscopes, staplers, etc.) can be guided through a lumen of the cannula of the trocar. For example, the tool drive 206 may include an elongated base (or "stage") 208 and a tool carriage 210, which is slidingly engaged with the elongated base or stage 208. The stage 208 may be configured to couple to the distal end of a robotic arm 200 such that articulation of the robotic arm 200 positions and/or orients the tool drive 206 in space. The tool carriage 210 may be configured to receive a tool for extending through the associated cannula of a trocar. Additionally, the tool carriage 210 may actuate a set of articulated movements through a cable system or wires manipulated and controlled by actuated drives (the terms "cable" and "wire" are used interchangeably throughout this application). The tool carriage 210 may include different configurations of actuated drives, such as a mechanical transmission. The plurality of the joint modules 204A-204E of the robotic arm 200 can be actuated to position and orient the tool drive 206 for robotic surgeries.

Figure 3:
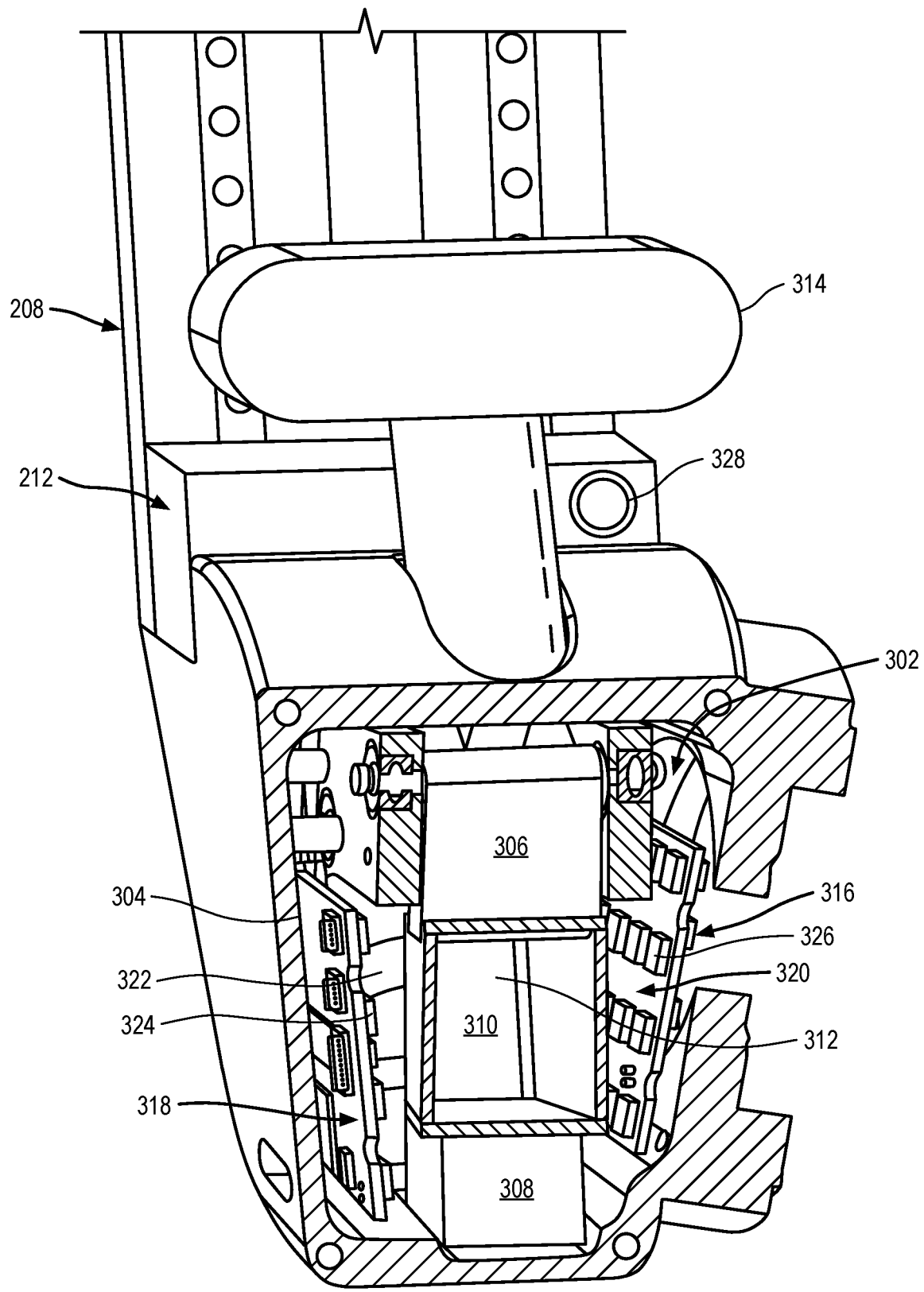
FIG. 3 is a schematic perspective view of an attachment device of the robotic arm of FIG. 2.

Referring additionally to FIG. 3, FIG. 3 illustrates a magnified perspective view of an attachment device associated with a robotic arm (e.g., docking interface 212 of robotic arm 200). As will be described in more detail in reference to FIG. 4A-4B, a cannula can be coupled to the tool drive 206 or another component of the surgical robotic system 100 at the attachment device or docking interface 212 located at a distal block of the elongated base 208. The attachment device or docking interface 212 is configured to receive a portion of the cannula (e.g., cannula lug). The attached device or docking interface 212 may be referred to interchangeably herein as a cannula or trocar docking interface, attachment device, or mounting device. The docking interface 212 can provide a reliable and quick way to attach the cannula to the surgical robotic system 100.

The attachment device or docking interface 212 can define a chamber 302 that is accessible through a mouth or frontal opening 304 of the docking interface 212 and which can include first and second clamp components 306, 308 (e.g., arms, plates, levers, members) arranged about a receiver 310 that defines a receiving space 312 for receiving a portion of the trocar or cannula (e.g., a cannula lug in a proximal portion of the cannula). At least one of the clamp components 306, 308 may be pivotable between an open position and a closed position such that an attachment portion of the cannula (e.g., cannula lug) can be inserted into the receiving space 312 between the clamp components 306, 308 so that a portion of the cannula is held in place at least partially by the first and second clamp components 306, 308.

In one variation, the attachment device or docking interface 212 may include an over-center mechanism such as an actuator, latch or lever 314 or other suitable locking component that mechanically cooperates with the clamp component 306, for example, through a pin and slot arrangement or through another pivotable or movable connection, between the open and closed positions. The lever 314 may be coupled to, or otherwise assist with locking the device in an open or closed position, and may therefore also be referred to herein as a locking assembly or component, or be considered part of a locking assembly or component. The actuator or lever 314 can be movable between a forward, locked position (e.g., a locked over-center position) and a rearward, unlocked position. When the actuator or lever 314 is moved toward the locked position, the lever 314 may urge the clamp component 306 downwardly toward the receiving space 312 and lock the clamp component 306 in the closed position such that a portion of the cannula (e.g., a cannula lug) is securely held between the first and second clamp components 306, 308. In some variations, second clamp component 308 can be stationary or can be fixed. In one variation, the actuator or lever 314 can be controlled and/or driven manually or automated, or a combination of manually and automated. Representatively, in some aspects, the attachment device may include a fully mechanical locking assembly that locks the clamp in the open position (e.g., a lock-out position) and then automatically transitions to a closed position (e.g. locked position) upon detecting that the cannula is inserted into the clamp in the proper position. The specific configuration of the locking component(s) and its operation will be described in more detail in reference to FIG. 4A-4B.

In some variations, the attachment device or docking interface 212 may also provide a sterile barrier between sterile components such as the cannula and non-sterile components such as the first and second clamp components 306, 308 (or other non-sterile components of the surgical system). The sterile barrier may be provided, for example, by a sterile adapter interposed between the cannula and the first and second clamp components 306, 308 (as described in more detail in reference to FIG. 11A-11D)

In some aspects, the attachment device or docking interface 212 may also include a sensor system 316. The sensor system 316 may be used to detect, for example, a characteristic of the cannula positioned within the docking interface 212 as will be described in more detail in reference to FIGS. 6-7 and/or FIGS. 10A-10B. The sensor system 316 may include a motherboard or first sensor board 318 at a first location of the docking interface 212 and a daughterboard or second sensor board 320 at second location of the docking interface 212 and in electrical communication with the first sensor board 318 via a cable 322 or other electrically conductive connection. In one variation, communication between the sensor boards 318, 320 can employ a multi-slave and multi-master inter-integrated communication computer bus. One or both of the sensor boards 318, 320 can include a microprocessor or other associated processor, for example, to control and/or read the sensors of the sensor boards 318, 320 and to facilitate communication between the sensor boards 318, 320, e.g., to enable temporal synchronization between the sensor boards 318, 320. As shown, the first sensor board 318 and the second sensor board 320 are positioned spaced apart from but parallel to each other, e.g., facing each other, on opposite lateral sides of the chamber 302 of the docking interface 212. The first sensor board 318 includes may include a first plurality of sensors 324 and the second sensor board 320 may include a second plurality of sensors 326. For example, the sensors 324, 326 may be embedded in or otherwise coupled to the robotic arm 200 or the tool drive 212. Each of the plurality of sensors 324, 326 may be arranged such that at least one sensor 324, 326 is disposed rearward, e.g., at a depth measured from the frontal opening 304 of the docking interface 212, with respect to another respective sensor 324, 326. While the sensors 324, 326 have been described in a grid-like configuration of rows, it will be understood that one or both of the pluralities of sensors 324, 326 can have a different arrangement without departing from the disclosure.

As described further herein, the sensors 324, 326 may be operable to sense or measure a magnetic field associated with the cannula inserted therein, and produce respective corresponding electrical signals. In this regard, the sensors 324, 326 can be configured as magnetometers, e.g., sensors that receive at least a portion of a magnetic field as an input and produce an output electrical signal corresponding to a strength or other characteristic of the magnetic field, and such that the sensors 324, 326 can be transducers. Any of the sensors 324, 326 can be configured to receive a different physical input and produce a corresponding electrical signal, for example, inertial measurement units, accelerometers, etc. In this regard, the sensors 324, 326 produce an output electrical signal that can be electrically communicated to, for example, a processor or controller that is incorporated into the control tower to provide force or velocity commands to direct a movement of the robotic arm (e.g., robotic arm 200) via the robotic arm actuators (e.g., actuators 117), as described further herein. It will be understood that a processor can be incorporated into additional or alternative portions of the surgical robotic system 100, and that the sensor system 316 can be in electrical communication with one or more different processors. For example, a switch 328 or other control is mounted on or near the docking interface 212, for example, behind the actuator or lever 314 at a position such that the actuator or lever 314 can be urged into contact with the switch 328, as described further herein. The switch 328 can be in electrical communication with the processor in the control tower to signal the processor to energize or activate one or both of the sensor boards 318, 320 to activate the sensor system 316 to sense or measure magnetic fields, and to effect guidance of the robotic arm toward the cannula according to an algorithm, as described further herein. In one variation, the sensor system 316 can be activated by the processor prior to or independently of the action of the switch 328, and the switch 328 can be used to signal the processor to begin calculations based on the signals received from the sensor system 316 to determine the estimated pose of the cannula and then affect guidance of the robotic arm 200 and its coupled tool drive 206. The switch 328 can have one of several different configurations, e.g., a mechanical button and mechanical switch combination may be preferred but another form of tactile interface or a touchscreen is also possible, that can be activated by a user.

While the sensor boards 318, 320 have been generally described as respective first and second printed circuit boards (PCBs) including the respective sensors 324, 326 embedded therein or thereon, it will be understood that the sensor system 316 can be provided in a different arrangement, for example, as discrete components, without departing from the disclosure. Additionally, it will be understood that any of the components described herein can be in communication via wired and/or wireless links, using any suitable ones of a variety of data communication protocols.

Figure 4A:
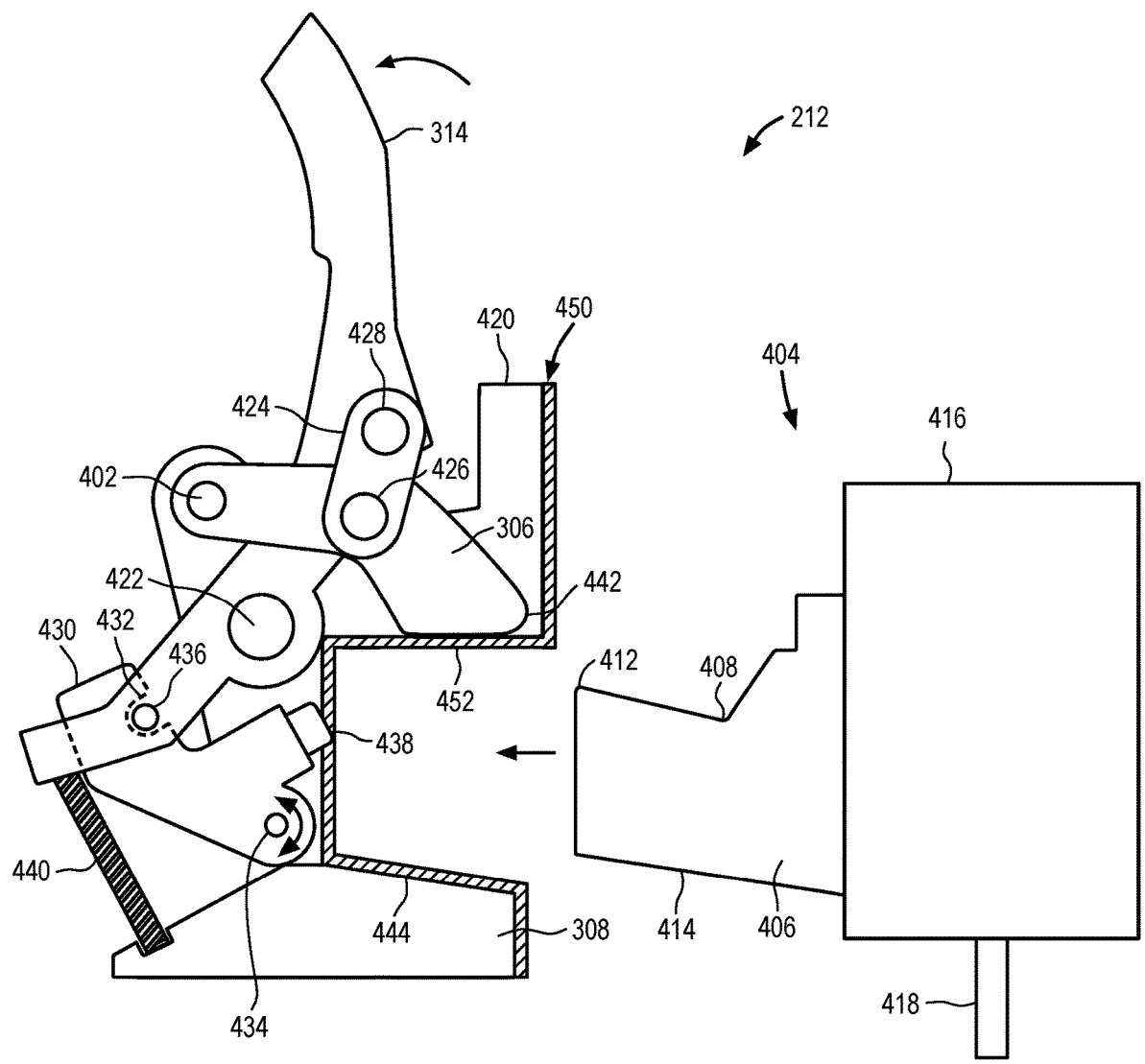
FIG. 4A is a cross-sectional side view of the attachment device of the robotic arm of FIG. 2 in an open position.
Figure 4B:
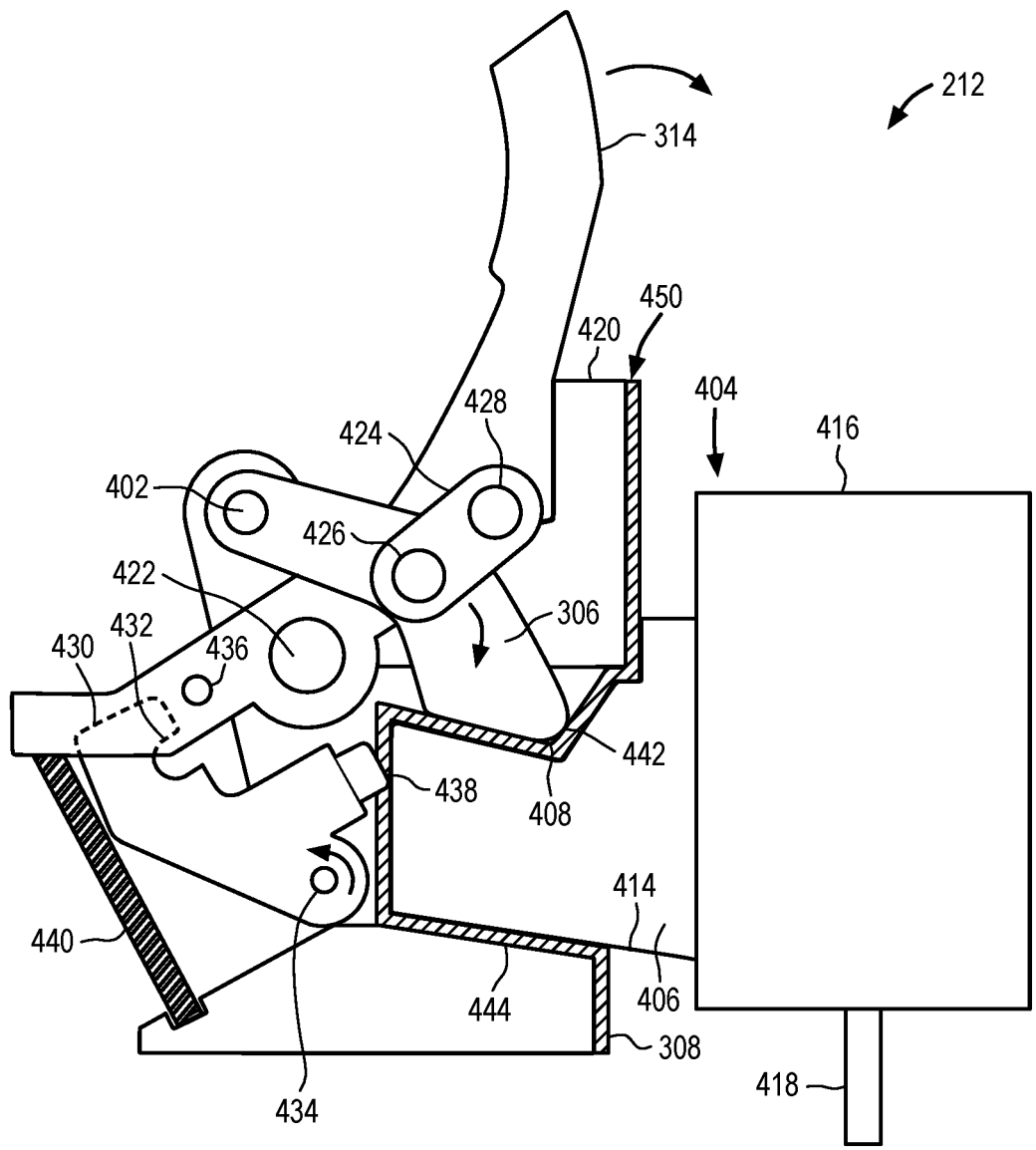
FIG. 4B is a cross-sectional side view of the attachment device of the robotic arm of FIG. 2 in a closed position.

Aspects of the attachment device or docking interface, and its operation, will now be described in more detail in reference to FIGS. 4A-4B. Representatively, as can be seen from FIG. 4A-4B, the attachment device or docking interface 212 may include first and second clamp components 306, 308 which define an opening 304 (e.g., receiving space or chamber) for receiving a cannula 404. The latch, actuator or lever 314 for transitioning the first and second clamp components 306, 308 between the open position (allowing for insertion of cannula 300 between clamp components 306, 308) and closed position (locking or clamping the cannula 300 between clamp components 306, 308) is also provided. Representatively, the first clamp component 306 may be moveable or pivotable about a clamp pivot point 402 by the lever 314 between an open position, such as is shown in FIG. 4A, and a closed position, such as is shown in FIG. 4B. In some aspects, the second clamp component 308 may be fixed or stationary. In other variations, the second clamp component 308 may be pivotable similar to the first clamp component. The second clamp component 308 may be spaced from the first clamp component 306 to form the opening 304 configured to receive a portion of the cannula 404 such as, for example, an attachment portion or cannula lug 406 of the cannula 404.

The two clamp components 306, 308 may be supported on a support component 420 such as, for example, a plate, bar, beam, or other suitable surface of a tool driver in a robotic surgical system. The first clamp component 306 may be supported on the support component 420 at a first location via the first pivot point 402 (e.g., pin joint, hinge, etc.), and the second clamp component 308 may be supported on the support component 420 at a second location spaced from the first clamp component 306. In some variations, the first clamp component 306 can be attached to a pivoting structure that allows the first clamp component 306 to rotate about the pivot point 402, and the pivoting structure can be attached to the support component 420. In such variations, the first clamp component 230 can be attached to the pivoting structure via a fastener (e.g., bolt, nail, screw, pin, etc.) or an adhesive (e.g., epoxies, polyurethanes, polyimides, etc.), and/or via other fastening techniques including, for example, crimping, welding, brazing, etc. In other variations, the first clamp component 306 can be integrally formed with a pivoting structure such as, for example, a living hinge. In some variations, the second clamp component 308 can be directly attached to the support component 420 via a fastener (e.g., bolt, nail, screw, pin, etc.), an adhesive (e.g., epoxies, polyurethanes, polyimides, etc.), and/or other fastening technique (e.g., crimping, welding, brazing, etc.). In other variations, the second clamp component 308 can be integrally formed with the support component 420. In some variations, the two clamp components 306, 308 can be formed of a plastic, a metal, or a composite material. In some variations, the two clamp components 306, 308 can be formed via machining, molding, or other manufacturing techniques. Although the variation shown generally depict two opposing clamp components, it should be understood that in other variations, the attachment device may include more than two clamp components.

In some aspects, the two clamp components 306, 308 may be non-sterile and the cannula 404 may be sterile. Thus, a sterile adapter 450 can be provided that separates the non-sterile clamp components 306, 308 from the sterile cannula 404. As depicted in FIGS. 4A-4B, a sterile adapter 450 may form a sterile barrier between the non-sterile clamp components 306, 308 and the sterile cannula 404. The sterile adapter 404 can be a cover that has an opening 452 for receiving the attachment portion 406 of the cannula 404 such that, the attachment portion 406, when received in the sterile adapter 450, is covered or surrounded by the sterile adapter 450. The sterile adapter 450 may be sufficiently flexible in certain portions such that it can deform (e.g., receive the attachment portion 406 when the attachment portion 406 is inserted through the opening) but have sufficient stiffness in other portions such that it retains a non-deformed or resting shape that generally corresponds to a shape of the attachment portion 406 of the cannula 404. The particular configuration of the sterile adapter 450, including both flexible and rigid portions, will be described in more detail in reference to FIGS. 11A-11D.

The sterile adapter 450 may be releasably mounted to the base member 420 such that it can be replaced as necessary. For example, the sterile adapter 450 may include an engagement mechanism that latches onto an edge or ridge of the base member 420 (or other support member coupled to the base member 420).

As further shown, cannula 404 may have a proximal portion 416, such as, for example, a hub, fitting, connector, etc. The proximal portion 416 of the cannula 404 may include the attachment portion 406. The attachment portion 406 may extend from a side of the proximal portion 416 and be configured for insertion within the opening 304 of the attachment device or docking interface 212. The cannula 404 may also have a shaft 418 (partially depicted in FIGS. 4A-B) that extends from the proximal portion 416. The shaft 418 may have a lumen through which one or more surgical instruments may be inserted. When the cannula 404 is disposed in a patient, a distal end of the shaft may be positioned within the patient's body such as, for example, in a body cavity.

To enable a robotic surgical procedure to commence, the surgical robotic arm must be docked to the cannula. Therefore, at some point in the workflow, the surgical staff will bring the surgical robotic arm in the sterile field to gain access to the surgical field. During this operation, the robotic arm (on a surgical table or on a cart) is manually or autonomously guided toward the surgical port (incision) by the surgical staff or the surgeon. The goal is to "dock" the surgical arm to the cannula to establish a rigid connection and then deploy surgical tools through the access channel. Due to the delicate nature of interacting with the surgical incision and the confined space in the operating room, this operation is typically carried out by one person with one hand on the robot and one hand on the cannula. This can be challenging because the user's ability to grab the arm is limited by the cannula position and the arm geometry. For example, the locking component (e.g., the lever or actuator) for locking the cannula to the arm may not be accessible in all configurations and the geometry of the arm might provide pinch points. The attachment device or docking interface 212 addresses some of these challenges by providing an improved configuration for attaching (e.g., docking) the cannula to the surgical robotic arm which allows a user to grab the arm anywhere he/she wants, and provides audible, tactile, and visual feedback on the success of the task.

Representatively, as previously discussed, the attachment device or docking interface 212 may include a fully mechanical locking assembly that locks the device (e.g., lever 314 and/or first clamp component 306) in the open position (e.g., a lock-out position) and then allows the device 212 to automatically transition to a closed position (e.g. locked position) upon detecting that the cannula is inserted into the clamp in the proper position. For example, the assembly may automatically transition through three states during docking of the cannula to the robotic arm. Representatively, the states may include 1) lock-out open position that allows the user to signal to the system that "docking mode" is process, 2) mechanical detection that the cannula is in the correct position for docking, and 3) automatic clamping of the cannula and signaling to the user that the cannula is attached.

To transition the attachment device 212 through these states, the device may include lever 314 as previously discussed, which may also be interchangeably referred to herein as a locking component or actuator. The lever or locking component 314 may be moveably coupled to the base 420 and the first clamp component 306. For example, the lever or locking component 314 may be coupled to the base 420 and move relative to the base at pivot point 422. The lever or locking component 314 may further be coupled to the first clamp component 306 by a link 424 including pivot points 426, 428 which allow the locking component 314 and the first clamp component 306 to move relative to one another. For example, as shown in FIG. 4A, when in the open (e.g., lock-out open position), the lever or locking component 314 is pivoted about pivot point 422 to a rearward position (e.g., away from base 420). Due to the coupling of the locking component 314 to the first clamp component 306 by link 424, this movement, in turn, causes the first clamp component 306 to pivot about the pivot point 402 in an upward direction (e.g., away from the opening 304). In this aspect, the locking component 314 and/or the first clamp component 306 are in the open position and the cannula 404 can be inserted into the opening 304.

As previously discussed, the locking component 314 and first clamp component 306 are held (or locked) in this open position (e.g., the lock-out open position) until the cannula 404 is properly inserted into opening 304. In this aspect, the device may further include a lock out mechanism 430 to hold or lock the locking component 314 and first clamp component 306 in this open position (e.g., the lock-out open position) until it mechanically detects proper insertion of the cannula. For example, the lock out mechanism 430 may be a trigger like mechanism that includes a hook 432 at one end and another end that is pivotally coupled to the base 420 at a pivot point 434. The hook 432 is configured to hook around, or otherwise engage with, a bearing 436 attached to the lever or locking component 314 when the locking component 314 is in the open position, to hold the lever or locking component 314 (and first clamp component 306) in the lock-out open position. The lock out mechanism 430 may further include a protruding member 438, which when contacted by a cannula properly inserted and/or aligned within the opening 304, will cause the lock out mechanism 430 to disengage with the locking component 314. This, in turn, allows the locking component 314 to automatically transition to the closed position. For example, the protruding member 438 may be between the hook 432 and pivot point 434 and extend into the opening 304 when the lock out mechanism 430 is engaged with the lever or locking component 314 (e.g., hook 432 is around bearing 436). When the cannula lug 406 is inserted within the opening 304 as shown in FIG. 4B, the cannula lug 406 will contact and push the protruding member 436 away from the opening 304. This, in turn, causes the lock out mechanism 430 to pivot in a rearward direction and the hook 432 to disengage with, or otherwise release, the locking component bearing 436. The locking component or lever 314 may be biased toward the closed position (e.g. forward position) by a spring 440 such that when it is released from the lock out mechanism 430, it automatically pivots forward (e.g., closer to the base 420) to the closed position and attaches the cannula 404 to the robotic arm.

In some aspects, a proper docking position or alignment of the cannula 404 (e.g., cannula lug 406) relative to the attachment device or interface 212 must occur, or be otherwise detected, for the locking component 314 and/or clamping components 306, 308 to automatically transition from the lock-out open position to the closed position. A proper docking or alignment position means the cannula is in a position within the opening suitable for attachment to the surgical robotic system. An improper or misaligned position means the cannula is in a position within the opening that is not suitable for attachment to the surgical robotic system. For example, for the cannula 404 to be inserted far enough into opening 304 for the cannula end 412 to contact and disengage the lock out mechanism 430 from the lever 314 as previously discussed, the cannula 404 must be in the proper docking or alignment position within opening 304. If the cannula 404 is not in the proper docking position or misaligned, the lock out mechanism 430 will not disengage and the locking component 314 and/or clamping component 306 will remain in the lock out position until a proper alignment or docking position is detected. The proper docking or alignment position of the cannula may therefore be considered mechanically detected by the system (e.g., detected by the attachment device or interface 212) when the cannula lug 406 contacts, or otherwise causes, the lock out mechanism 430 to disengage from the lever 314. For example, in some aspects, the attachment device or interface 212 may include a particular shape and/or surface feature that only mates with the cannula 404, and allows the cannula 404 to disengage the lock out mechanism 430 from the lever 314, when the cannula is in the docking position or otherwise properly aligned within the opening 304. In further aspects, the cannula 404, more specifically the cannula lug 406, may be considered to have a particular shape and/or surface feature that only mates with the attachment device or interface 212, and allows the cannula 404 to disengage the lock out mechanism 430 from the lever 314, when the cannula lug 406 is in a docking position or otherwise properly aligned within opening 304.

Representatively, in some aspects, the second clamping component 308 may have an alignment structure 444 which is in the shape of a sloped surface. The alignment structure 442 may be capable of mating with, or otherwise being aligned with, a complimentary shaped alignment structure 414 (e.g. sloped surface) on the bottom side of the cannula lug 406. The alignment structures 444, 414 will be described in more detail in reference to FIGS. 10B-10C.

In still further aspects, the first clamping component 306 may include an alignment structure 442 which forms a triangular protrusion. The alignment structure 442 may be capable of mating with, or otherwise being aligned with, a complimentary shaped alignment structure 408 (e.g., recessed region) on the top side of the cannula lug 406. For example, the cannula 404 may be moved in a direction of the arrow such that the attachment portion 406 of the cannula 404 is inserted into the region between the two clamp components 306, 308 or, more specifically, inserted through the opening 304 which is located in the region between the two clamp components 306, 308. In some variations, the surface of the first clamp component 306 may be configured to help guide and orient the attachment portion 406 when it is inserted into the region between the two clamp components 306, 308. For example, the surface of first clamp component 306 may be angled such that it smoothly receives the attachment portion 406 when the attachment portion 406 is inserted into the region between the two clamp components 306, 308 in the predefined orientation shown in FIG. 4A (e.g., in an orientation where the structure 408 is facing the structure 442 to allow for engagement between the interfacing surfaces). When the attachment portion 406 is inserted into the region between the two clamp components 306, 308 in a different orientation, the structure 442 may push against or otherwise interfere with the attachment portion 406 to indicate that the attachment portion 406 is not properly orientated with respect to the two clamp components 306, 308. For example, the structure 442 may prevent the attachment portion 406 from being inserted into the region between the two clamp components 306, 308 (e.g., by creating a clearance that is too small for the attachment portion 06 to be inserted into the region) when the attachment portion 406 is not being inserted into the region between the two clamp components 306, 308 in the predefined orientation. In some variations, to help guide the attachment portion 406 into the opening 304 between the two clamp components 306, 308, the structures 442, 408 may have complimentary angles that mate with one another only when the attachment structure 406 is inserted into opening 304 at a single orientation (e.g., the proper docking and/or alignment position).

In some aspects, the alignment structures 408, 414 of the cannula lug 406 may be different such that the lug 406 is considered to have an asymmetrical shape which allows it to fit within the attachment device 212 in only one position. In this aspect, when it is detected that the cannula lug 406 is in the proper docking or aligned position within opening 304 (as shown in FIG. 4B), the device 212 automatically closes and clamps onto the cannula 404. This, in turn, solves an important surgical workflow problem by providing a fully mechanical and safe solution to docking a cannula to a robotic arm when access to the mechanical lever is difficult or impossible. Additional alignment structures and configurations will be described in more detail in reference to FIGS. 10A-10C.

Figure 5:
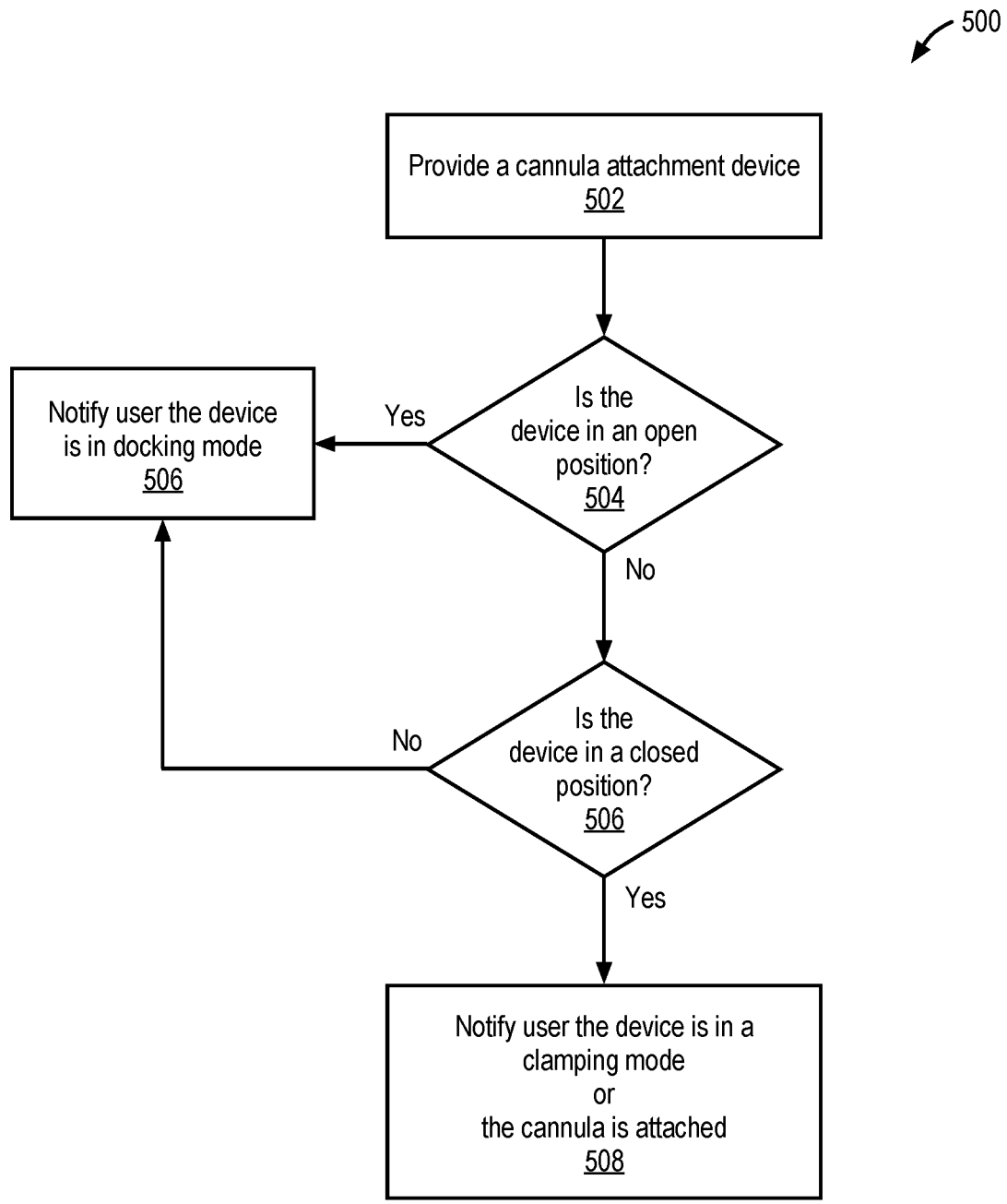
FIG. 5 is a process flow diagram of a method for providing user feedback relating to the attachment device of the robotic arm of FIG. 2.

In some aspects, upon mechanically detecting that the cannula 404 is in the proper docking position and/or that the device 212 has transitioned to the closed position, the system may further signal to the user that the cannula is in the docking position and/or the cannula is attached. For example, one or more of the previously discussed sensors (e.g., sensor system 316 or switch 328) may detect that the device 212 is in the closed position and signal to the user that the cannula is attached. In addition, the system may signal to the user whether the device 212 is in a docking mode or a clamping mode based on whether the device 212 is in the lock out open position or the closed position. The signal may be in the form of a message or other indicator on the system display, audio feedback, haptic feedback or any other suitable notification to indicate the state or mode of the system (or change in state or mode of the system) to the user. FIG. 5 illustrates an exemplary process flow for indicating to the user the state or mode of the device 212. Representatively, the process 500 may include providing a cannula attachment device (e.g., 212) at operation 502, and then determining whether the device is in an open position at operation 504. For example, the device 212 may be determined to be in an open position if, for example, the lever 314 or first clamping component 306 is in an open position. If the device is determined to be in an open position, the user is notified at operation 506 that the device is in the docking mode. In other words, the user may still be positioning the cannula within the device opening and/or the cannula may be in the opening but not yet properly aligned. If the device is not in the open position, the process continues on to determine whether the device is in the closed position at operation 506. For example, the device 212 may be determined to be in a closed position if, for example, the lever 314 or first clamping component 306 is in the closed position. If the device is determined to be in the closed position, the user is notified at operation 508 that the device is in the clamping mode or that the cannula is attached. If the device is still not determined to be in the closed position at operation 506, this may mean that the user is still trying to properly position the cannula in the device therefore the process returns to operation 506 and notifies the user that the device is in the docking mode.

Figure 6:
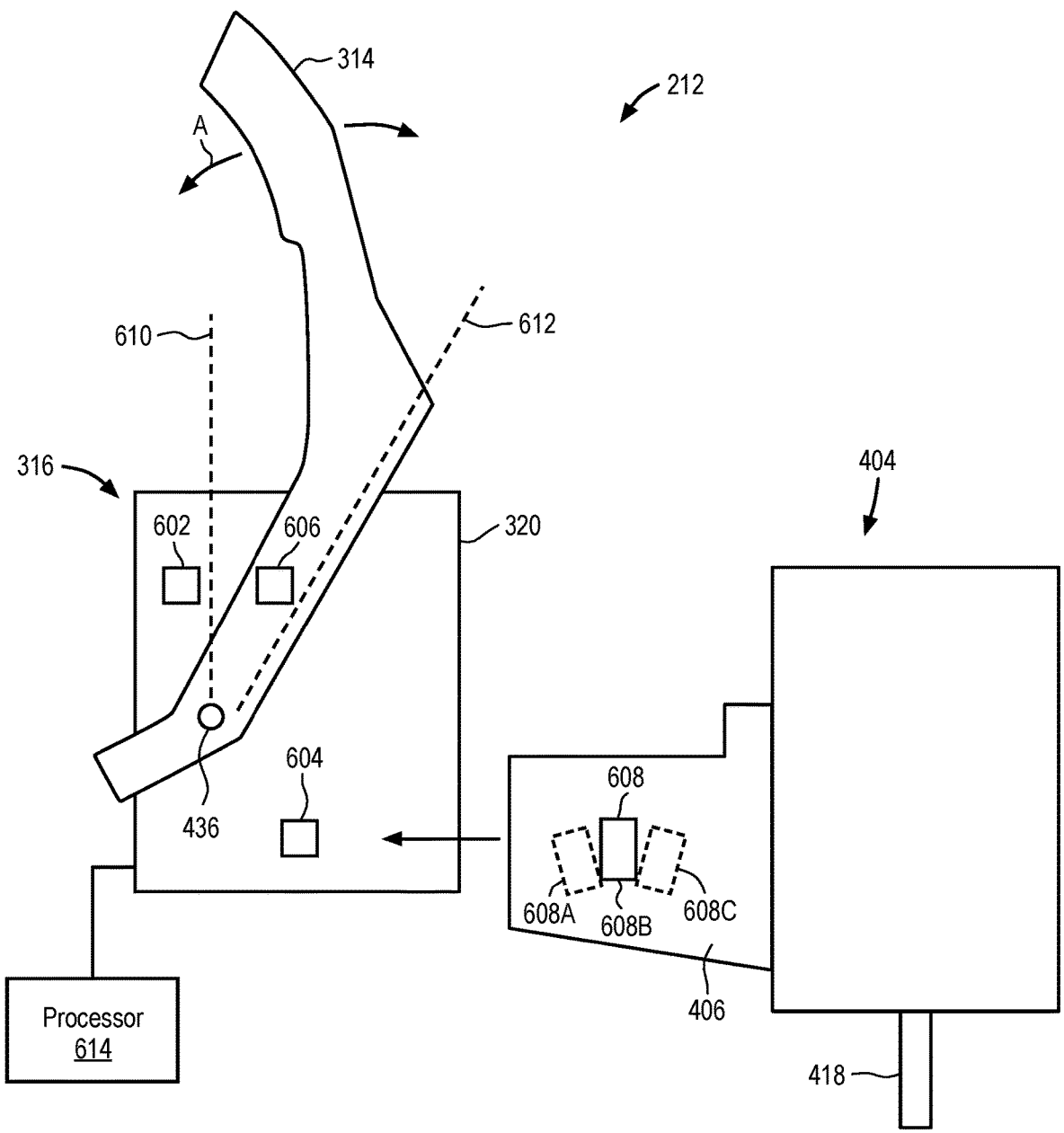
FIG. 6 is a cross-sectional side view of a sensor assembly associated with the attachment device of FIGS. 4A-4B.

In still further aspects, the attachment device or docking interface may include additional aspects that allow for detection of the presence of the cannula, proper latching onto the cannula, an angle of the lever, the type of cannula that has been attached or docked, and/or any scenarios that could indicate cannula release. For example, sensors that drive a finite state machine to detect any one or more of the previously mentioned scenarios or characteristics may be integrated into the device 212 and/or the cannula 404. Each of these states can then be communicated to the user using visual, audio, or other forms of feedback on the robotic arm, as well as via any form of similar feedback on the surgeon bridge. By way of background, it should be understood that when docking a surgical robotic arm to a cannula there needs to be an accurate way to sense that the cannula is: (1) properly docked to the arm with the attachment device completely closed; (2) to detect which type of cannula has been docked and communicate that to the system (e.g., Standard/Bariatric, 8 mm/12 mm); and (3) to monitor if the cannula is somehow released or becomes undocked. In this aspect, FIG. 6 illustrates a schematic diagram of one representative sensor arrangement for detecting any one or more of the previously mentioned scenarios or characteristics. Representatively, FIG. 6 illustrates at least one sensor 602 for detecting a characteristic of the locking component or lever 314 and at least one sensor 604 for detecting a characteristic of the cannula 404. In one aspect, the sensors 602, 604 may be magnet encoders and the lever 314 and the cannula 404 may include magnets 606, 608, respectively, that are detected by the encoders.

The characteristic of the locking component or lever 314 detected by the sensor 602 may be an angle of the locking component or lever 314. For example, any angle within the range of angle (A) may be detected. The angle of the locking component or lever 314 may further be used to determine, for example, whether the lever 314 is open or closed, the cannula is properly docked, or other characteristics associated with cannula attachment. For example, if the lever 314 is detected at angle 610, the system may determine the lever 314 is in the lock out open position. On the other hand, if the lever 314 is detected at angle 612, the system may determine the lever 314 is in the closed position. The angle may be measured relative to any point suitable for determining the lever position, for example the pivot point 436 or a center axis of lever 314.

Representatively, during operation, when the robotic arm is ready to be docked to a cannula, the lever 314 may be manually moved to the open position by the user and the lock out mechanism holds the lever 314 in the open position as previously discussed. A detection of this movement by sensor 602 may be used by the system to determine that a gravity compensated active back (GCAB) driving mechanism associated with the surgical robotic arm should be engaged to allow the robotic arm to be positioned at the docking interface or attachment device 212. Once the robotic arm is positioned and the cannula is pushed into the opening of device 212, the lockout is disengaged allowing the latch to close and secure the cannula to the arm as previously discussed. At this point the lever sensor 602 senses that the lever has been closed and has passed the mechanical over-center point (e.g., is at an angle corresponding to position 612). This information, may in turn, cause the system to disengage GCAB and hold the arm in that docked or attached position. The signal from sensor 602 may be actively monitored so that if the lever 314 is accidentally depressed after the cannula is attached, the system will transition to an error state that should stop the procedure and notify the user.

Referring now to the characteristics of the cannula 404 detected by sensor 604, representative characteristics may be, but are not limited to, (1) a presence of the cannula 404 within the device 212 opening and (2) a type of cannula. For example, the cannula 404 may be determined to be present when the cannula 404 is inserted into the opening such that the sensor 604 detects the magnet 608. The cannula 404 may be determined to be absent when sensor 604 does not detect the magnet 608. The presence (or absence) of the cannula 404 may also be used to determine, for example, whether the cannula is properly docked and/or released. For example, if the presence of the cannula is detected by the cannula sensor 604 and the lever is determined to be in the closed position based on information from the lever sensor 602, the system may determine the cannula is properly attached to the device (and the robotic arm). On the other hand, if the cannula presence is not detected by the cannula sensor 604 and the lever is determined to be in the open position based on information from the lever sensor 602, the system may determine that the cannula has been released or is not properly attached to the device (and the robotic arm).

The type of cannula may be detected based on the angle of the magnet 608 detected by sensor 604. In addition, sensing the magnetic orientation provides an additional datapoint that the cannula is present and stable within the device 212, but mainly serves to provide specific identification for the type of cannula that has been docked so that information can be communicated to the robotic system and to the user. For example, each type of cannula 404 may have a magnet positioned at a different angle as illustrated by magnets 608A, 608B, 608C. The angle may be, for example, an angle of the magnet's polar axis centerline relative to an orientation of magnet north pole. Therefore, when the sensor 604 detects the angled magnet 608A, angled magnet 608B or angled magnet 608C, the system can match the angled magnet that is detected up with the particular type of cannula it is associated with and notify the user of the cannula type. Representative magnet field orientations that can be detected by the sensors, and their respective cannula types that may be determined by the system, are shown in Table 1 as follows:

| Cannula Type | Magnet Field Orientation |
| --- | --- |
| Standard, 8 mm | 30 degrees ± 14.5 degrees |
| Bariatric, 8 mm | 90 degrees ± 14.5 degrees |
| Standard, 12 mm | 150 degrees ± 14.5 degrees |
| Bariatric, 12 mm | 210 degrees ± 14.5 degrees |

By monitoring the cannula type using sensor 604, there exists the opportunity to detect fake or incompatible cannulas as well as to sense a latching issue that might allow excessive movement of the cannula within the latching mechanism.

Moreover, the sensor 604 provides an additional signal that indicates that a certain magnetic threshold has been reached, which in turn, can be used to confirm the presence of cannula 404 in device 212. While this is also achieved by having a valid cannula type or identification reading as previously discussed, this signal is a more definitive binary value and may be the main signal used for cannula presence. Loss of this signal at any point in time may indicate a release of the cannula and may cause the system to transition to an error state that would stop the procedure and notify the user.

As previously discussed in reference to FIG. 3, sensors 602, 604 may be electrically connected to a sensor board 320 positioned within the device opening 304, or could be positioned in any location of device 212 suitable for detected the desired characteristics. The sensor board 320 can include a microprocessor or other associated processor 614, for example, to control and/or read the sensors 602, 604 of the sensor board 320, to facilitate communication of information from the sensors 602, 604 to the user, and to determine one or more of the previously discussed characteristics based on the sensor information. In addition, although sensor 604 is described as a single sensor that outputs two separate signals indicating cannula presence and type, different sensors for detecting each of these characteristics separately could be used. Still further, although only two sensors 602, 604 are illustrated, it is contemplated that at least four sensors or more may be used to provide redundancy for safety reasons.

Figure 7:
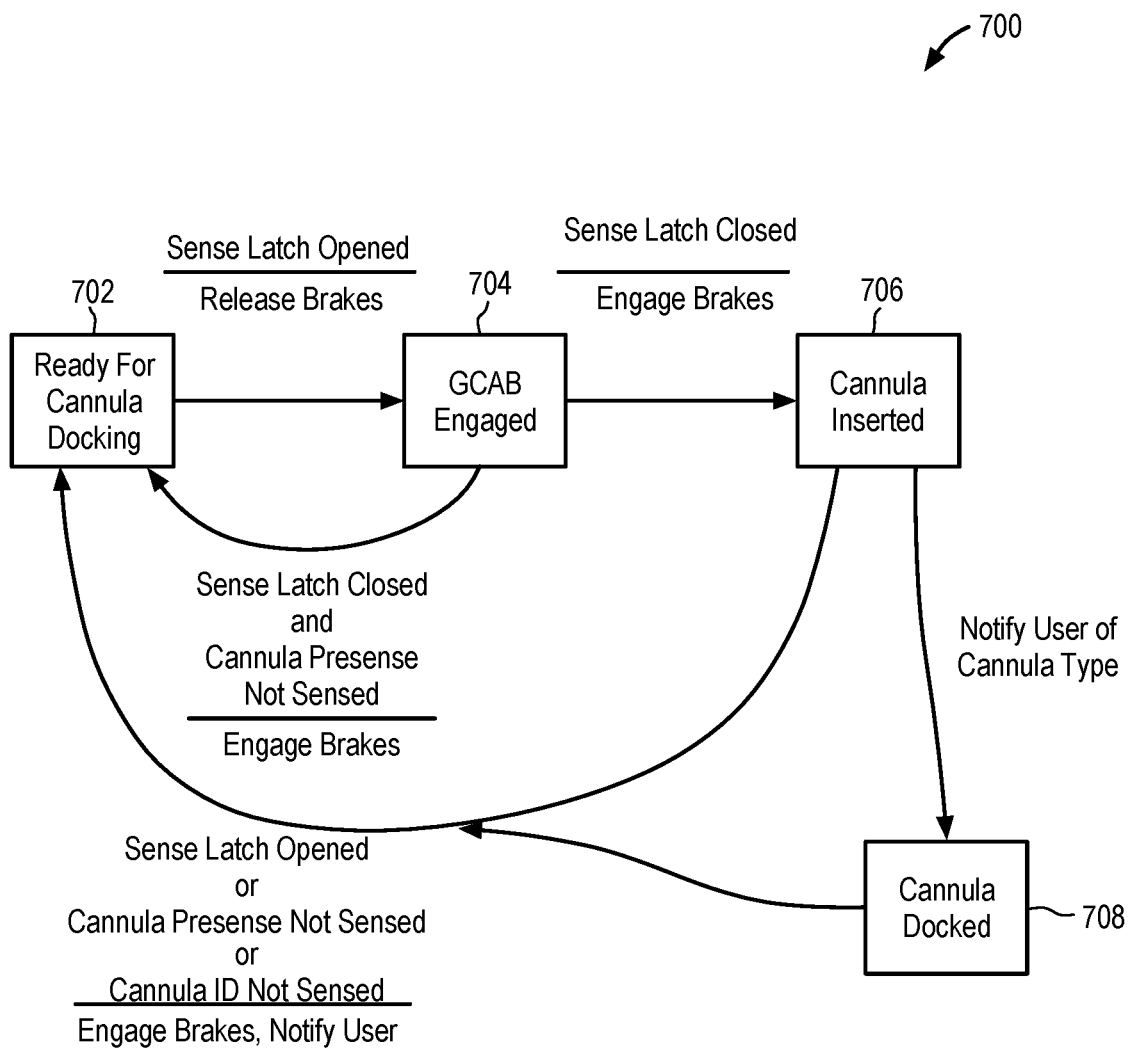
FIG. 7 is a process flow diagram of a method for detecting docking using the attachment device of the robotic arm of FIG. 2.

Referring now in more detail to the system operation based on the information detected by the previously discussed sensors, FIG. 7 illustrates one representative process. In one aspect, process 700 includes an initial state or mode in which the system is considered ready for cannula docking at operation 702. For example, the system may be considered ready for cannula docking when the system (e.g., a sensor) detects that the attachment device or interface device 212 is in the lock-out open position such that it is ready for cannula insertion (e.g., lever 314 is engaged with the lock out mechanism 430 and lever 314 and/or first clamp 306 is in the open position) and/or no cannula is determined to be present. Once it is determined the system is ready for cannula docking at operation 702, one or more associated processors may cause the surgical robotic system to disengage a braking assembly associated with a surgical robotic arm, and engage a gravity compensated active back ("GCAB") driving mechanism associated with the surgical robotic arm to allow for positioning of the cannula within a clamping assembly associated with a surgical robotic arm at operation 704. In addition, once GCAB is engaged, if the system (e.g., sensor assembly) detects a transition of the clamp assembly (e.g., a lever 314 or clamp 306 of attachment device 212) to the closed position and/or that the cannula is not present within the clamp assembly, the process returns to operation 702. For example, the one or more processors may cause the surgical robotic system to engage the braking assembly associated with the surgical robotic arm and disengage the GCAB driving mechanism associated with the surgical robotic arm so that a current position of the cannula relative to the clamping assembly is maintained. Alternatively, once GCAB is engaged, if the system (e.g., sensor assembly) detects a transition of the clamp assembly to the closed position and the cannula is present, the system determines that the cannula has been inserted into the clamping assembly and the one or more processors may cause the surgical robotic system to notify a user that the cannula is inserted at operation 706. In addition, once the cannula is detected and the system recognizes that it is inserted at operation 706, the system may further determine the type of cannula that was inserted and notify the user of the type of cannula. For example, the sensor assembly associated with the attachment device may determine the type of cannula based on a magnet orientation as previously discussed. Once it is determined at operation 706 that the cannula is properly inserted, the system may notify the user that the cannula is docked, or otherwise attached to the attachment or clamping assembly of the surgical robotic arm, at operation 708. In addition, if once it is determined at operation 706 that the cannula is inserted, but then the system senses that the clamping assembly is open, the cannula presence is not detected, or the cannula identifier (ID) cannot be detected, the system may engage the braking assembly and return to operation 702. In addition, the system may notify the user that the latch is now open and/or the cannula is not detected, therefore an error may have occurred and the procedure has been stopped. In other words, the system may notify the user that the system is ready for a cannula to be attached. In this aspect, the sensor assembly integrated into the attachment device (or clamping assembly) is used to drive a finite state machine to detect presence of the cannula, proper latching onto the cannula, the type of cannula that has been docked, and any scenarios that could indicate cannula release. Each of these states can then be communicated to the user using visual, audio, or other forms of feedback on the robotic arm, as well as via any form of similar feedback on the surgeon bridge.

Figure 8A:
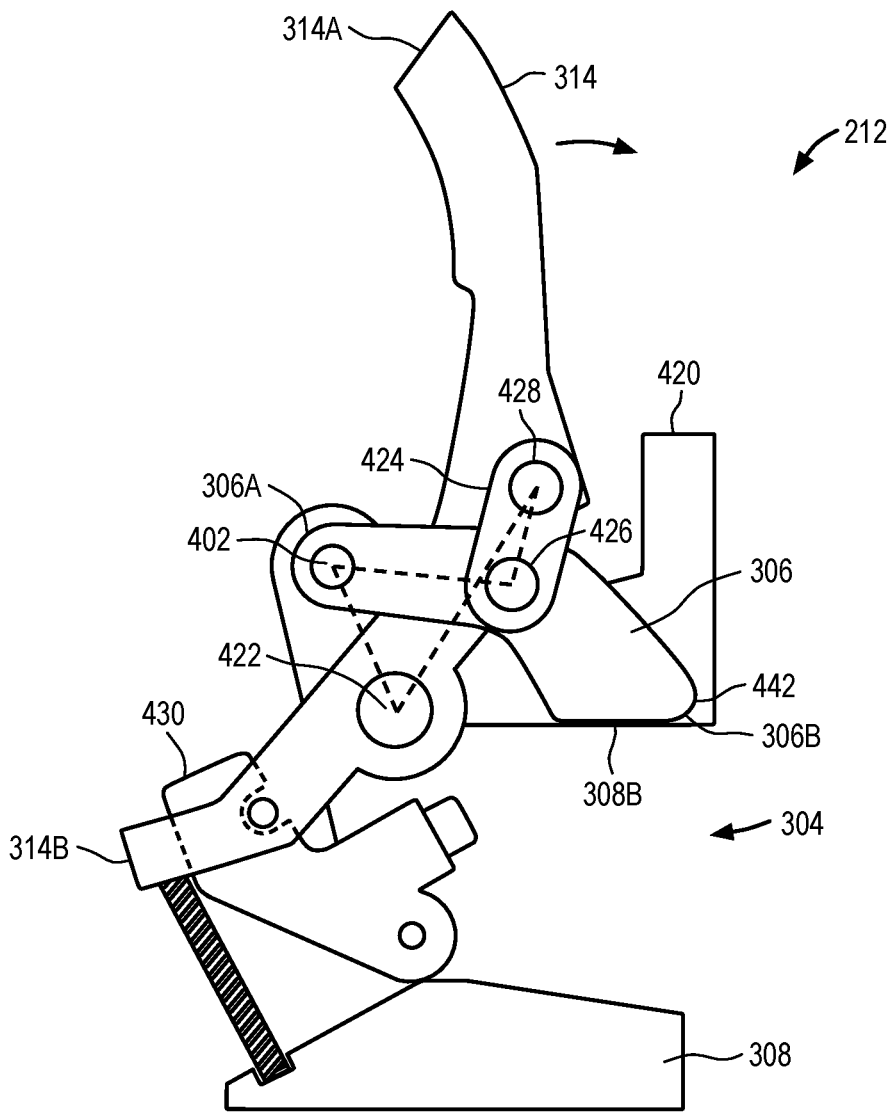
FIG. 8A is a cross-sectional side view of another aspect of the attachment device of FIGS. 4A-4B in the open position.
Figure 8B:
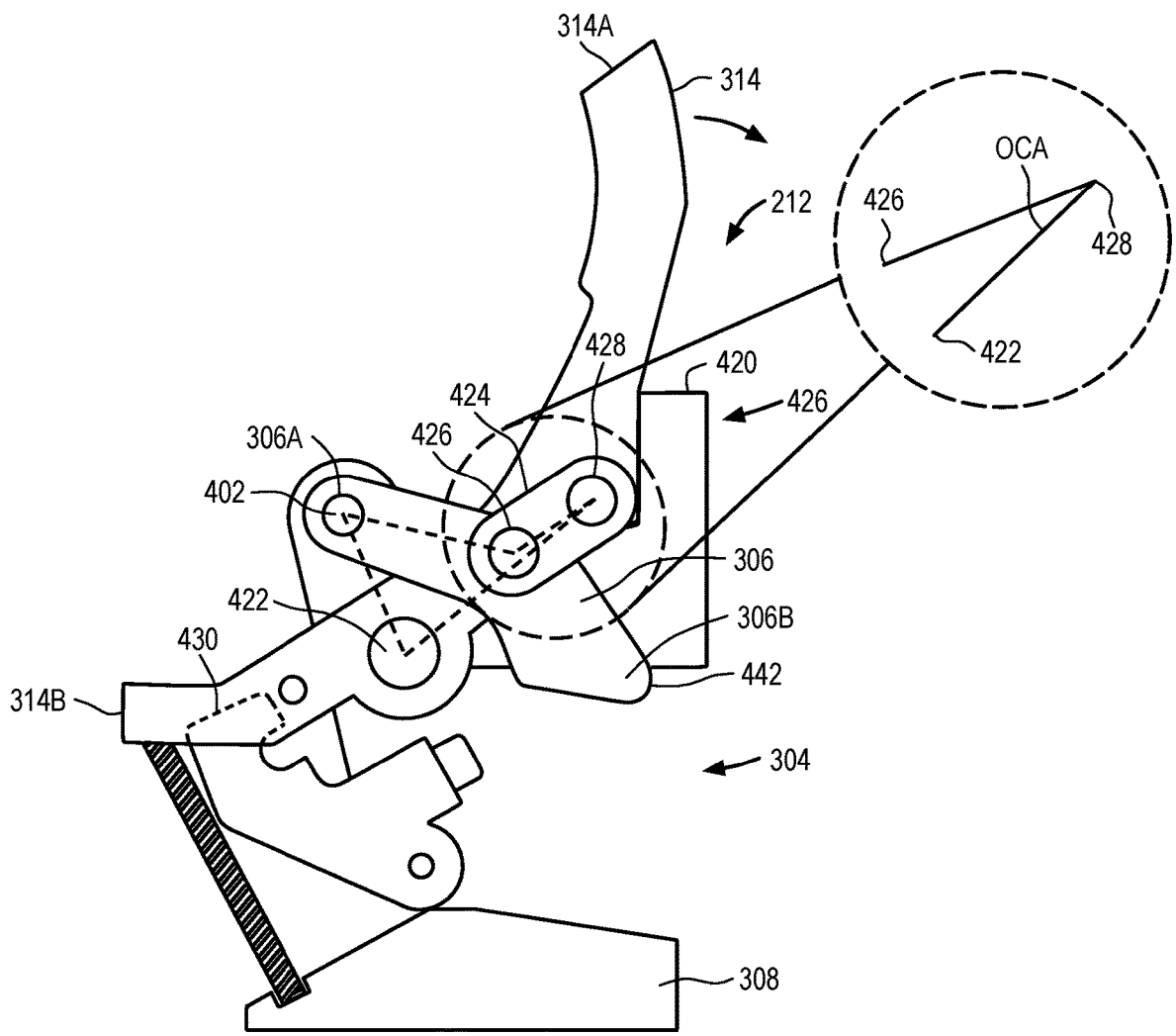
FIG. 8B is a cross-sectional side view of another aspect of the attachment device of FIGS. 4B-4B.

Returning now to additional aspects of the attachment device, FIGS. 8A-8B illustrates an over-center configuration of the attachment device. FIGS. 8A-8B illustrate the same attachment device or interface 212 described in reference to FIGS. 4A-4B, however the over-center configuration is now shown in more detail. The over-center configuration ensures a reliable and secure attachment of the cannula to the surgical robotic arm while also allowing a user to disconnect and reconnect the two items whenever necessary. For example, the over-center configuration may prevent the attachment or clamping mechanism (e.g., the lever) from being back driven to an open position by forces applied to the cannula. Once over center, the lever will increasingly force itself closed with any increasing load applied to the cannula. This helps to ensure the cannula is held securely and reliably to the robotic arm during surgery. Representatively, FIG. 8A illustrates the attachment device or interface 212 in the lock out open position as previously discussed in reference to FIG. 4A. In this open position, the attachment device or interface 212 is not considered to be in the over-center configuration. FIG. 8B illustrates the attachment device or interface 212 in the closed position as previously discussed in reference to FIG. 4B. For example, in the closed position, the actuator or lever is all the way forward resting against the base. For example, the actuator or lever pushes the first clamp component forward which then clamps the cannula lug against the second clamp component and holds it securely in the attachment device or interface 212. In this closed position, the attachment device or interface 212 is considered to be in the over-center configuration because the associated four bar linkage mechanism is designed to over-center.

Representatively, as previously discussed, attachment device or interface 212 includes a locking component, actuator or lever 314 that is movably connected to the base 420 at pivot point 422 near one end, which allows the other end of lever 314 to move between the open position (rearward position) and closed position (forward position). In one aspect, end 314A of lever 314 moves between the open/closed positions and may be manually controlled by the user. The pivot point 422 may be near the other end 314B of lever 314, which may be coupled to the lock out mechanism when the device is in the open lock out position. In addition, the first clamp component 306 is movably connected to the base 420 at pivot point 402 at one end 306A, which allows the other end 306B of the first clamp component 306 to move between the open (non-clamping) position and the closed (clamping) position. The lever 314 and the first clamp component 306 are also movably connected to each other by the link 424. The link 424 is connected to the lever 314 at pivot point 428 at one end and the first clamp component 306 at pivot point 426. In other words, the linkage mechanism of device 212 may include at least four pivot points 402, 422, 426 and 428 which form a four bar linkage mechanism. The linkage mechanism pivot points may therefore also be referred to herein as first pivot point 426, second pivot point 428, third pivot point 402 and fourth pivot point 422. During operation, at the beginning of the closing stroke (e.g., lever 314 moving in a forward direction toward base 420 as illustrated by the arrow), pivot point 426 (e.g., first pivot point) leads pivot point 428 (e.g., second pivot point) through the rotation of the mechanism. As the mechanism nears its fully closed position, pivot point 428 (e.g., second pivot point) overtakes pivot point 426 (e.g., first pivot point) as shown in FIG. 8B, at which point the attachment device 212 (e.g. lever 314) is said to be over-center. For example, in some aspects, the attachment device 212 may be considered to be fully closed (or latched) when pivot point 428 (e.g., second pivot point) is over center relative to pivot point 426 (e.g., first pivot point) by an over center angle (OCA) of one degree or less, or at least one degree. This particular over center angle (OCA) is critical to ensuring that the device does in fact over center, yet does not reach an over center angle that is so extreme that clamping force on the cannula lug begins to decrease. As previously discussed, as a result of this over center configuration, the attachment device will increasingly force itself closed (e.g., first clamp component 306) with any increasing load applied to the cannula.

Figure 9A:
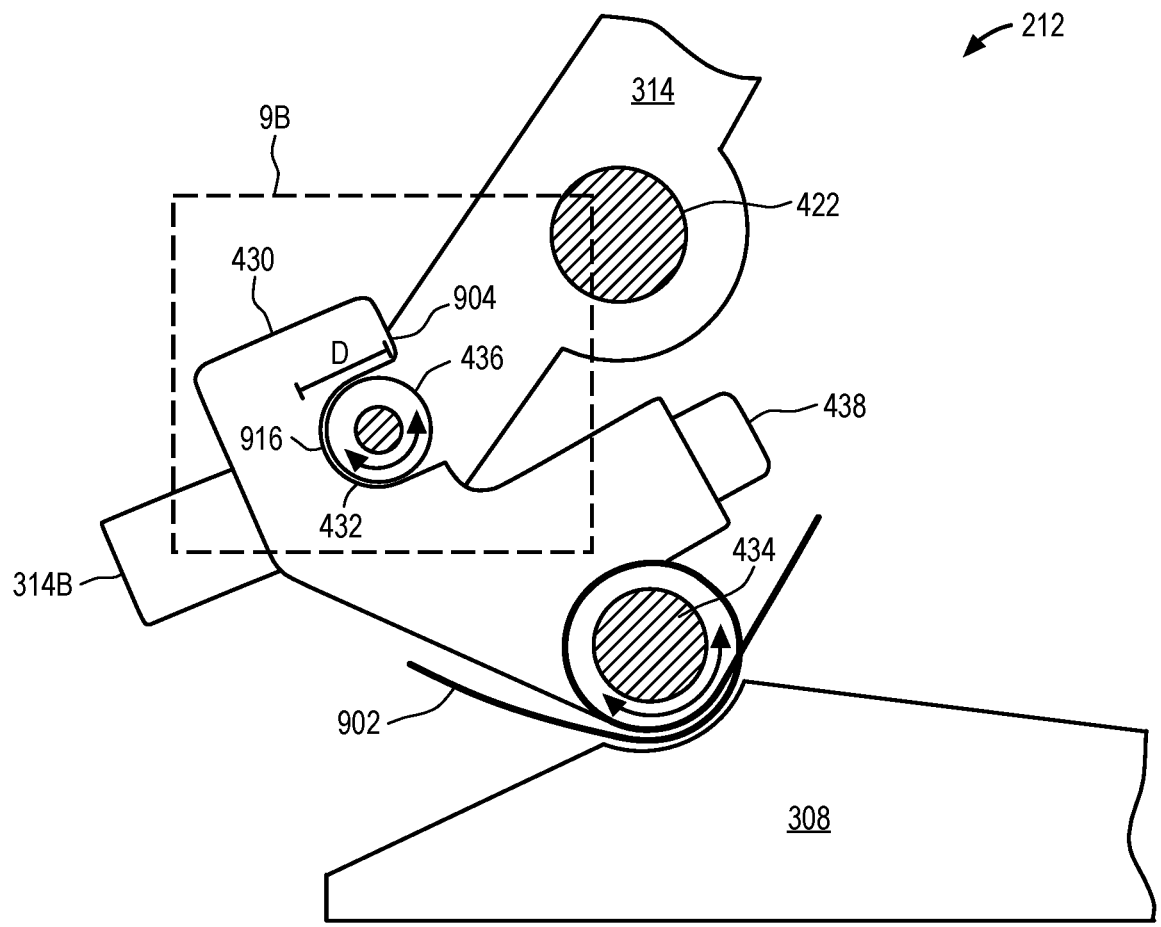
FIG. 9A is a cross-sectional side view of another aspect of the attachment device of FIGS. 4A-4B.
Figure 9B:
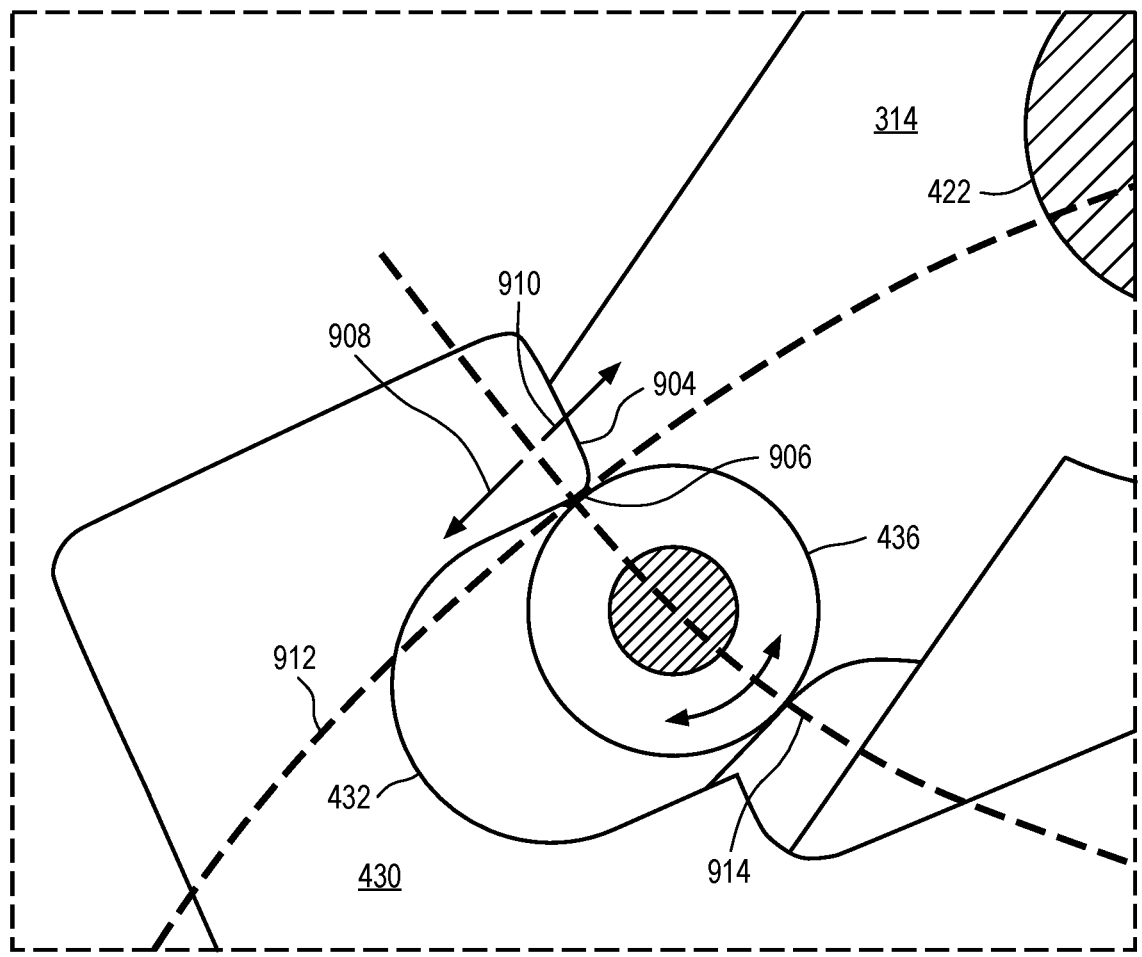
FIG. 9B is a magnified cross-sectional side view of a portion of the attachment device of FIG. 9A.
Figure 9C:
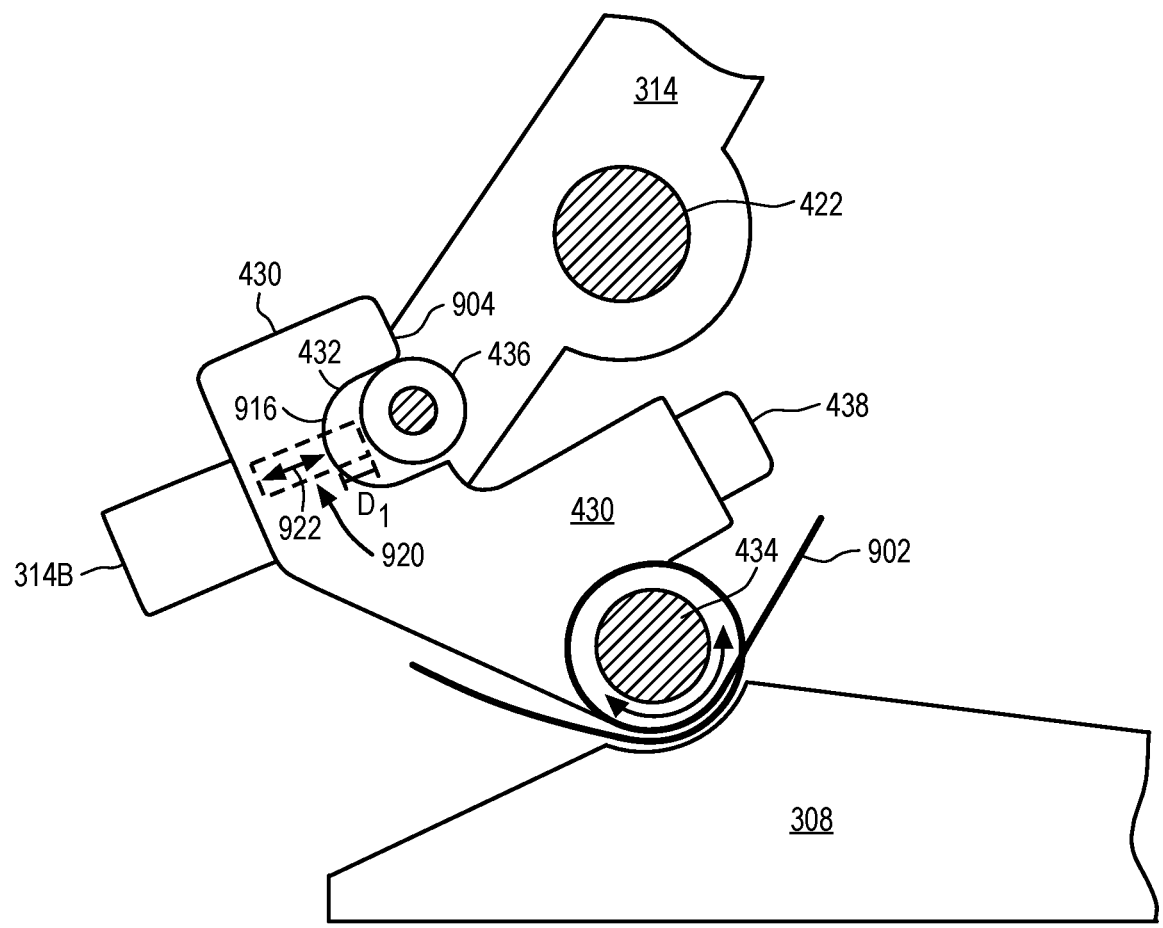
FIG. 9C is a cross-sectional side view of another aspect of the attachment device of FIGS. 4A-4B.
Figure 9D:
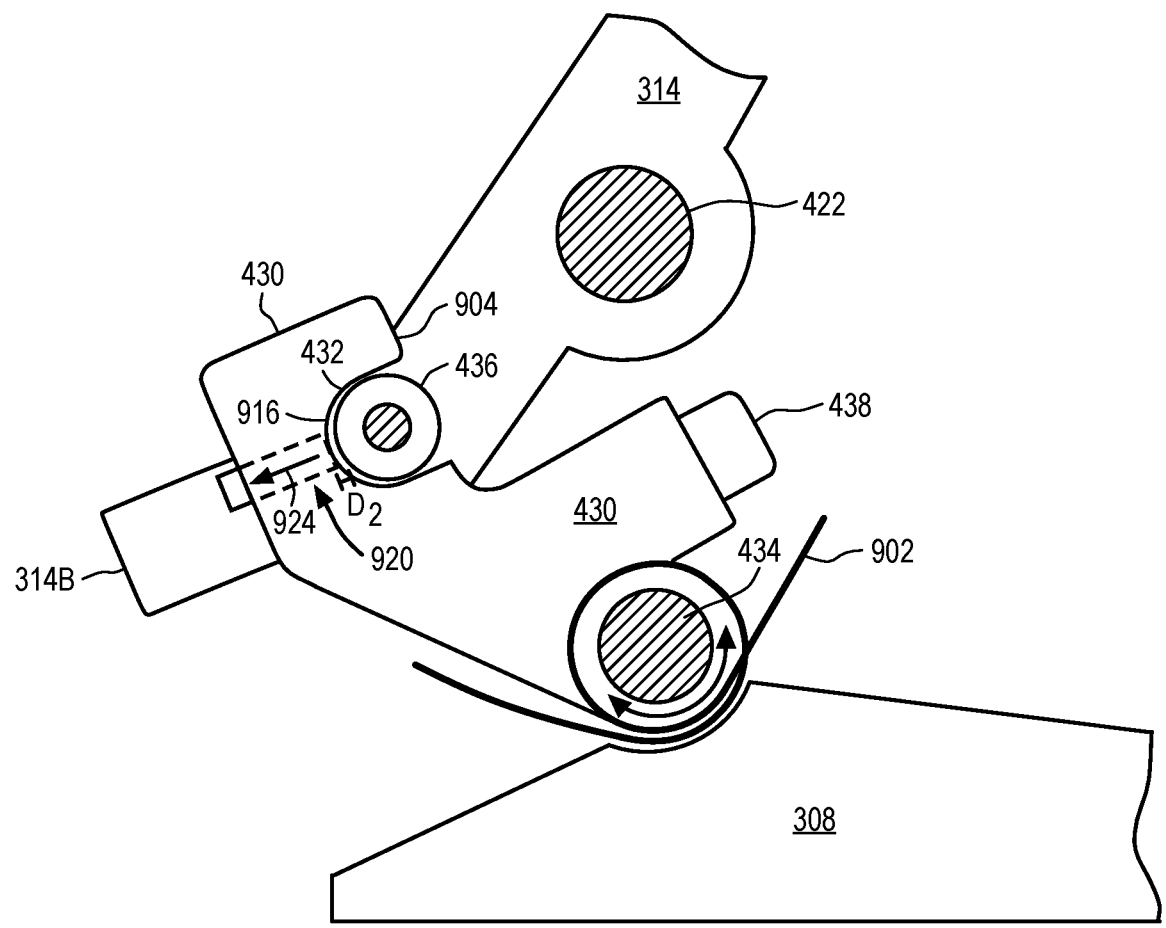
FIG. 9D is a cross-sectional side view of another aspect of the attachment device of FIGS. 4B-4B.

The lock out mechanism for holding the attachment device in the lock out open position will now be described in more detail in reference to FIGS. 9A-9D. Representatively, FIG. 9A-9B illustrate magnified cross sectional side views of the lock out mechanism, and FIGS. 9C-9D illustrate magnified cross sectional side views of an adjustment mechanism of the lock out mechanism of FIGS. 9C-9D. The lock out mechanism of FIGS. 9A-9D may be substantially the same as, and therefore include the same features as, lock out mechanism 430 described in reference to FIGS. 4A-4B. Certain features of the lockout mechanism may, however, be omitted from FIGS. 9A-9D for the sake of clarity.

Referring now in more detail to FIG. 9A, lock out mechanism 430 may be a trigger type locking mechanism which includes a hook 432 at one end and another end that is pivotally coupled to the attachment device base at pivot point 434. Hook 432 is configured to hook around, or otherwise engages with, the bearing 436 of the lever 314 to hold the lever 314 (and the associated clamping component) in the lock out open position. The lock out mechanism 430 further includes protruding member 438 between the hook 432 and pivot point 434, and a spring 902 at the pivot point 434. The spring 902 may bias the lock out mechanism 430 toward the lock out open position (e.g., a position in which hook 432 is hooked around bearing 436). The protruding member 438 may face the attachment device opening and be pressed by the cannula during insertion causing the lock out mechanism 430 to pivot as shown by the arrow at pivot point 434, and the hook 432 to unhook, or otherwise disengage with, the bearing 436 of the lever 314. This, in turn, allows the attachment device to automatically transition to the closed position because it is biased toward the closed position (e.g., the first clamp component to clamp onto the cannula), as previously discussed.

The lockout mechanism 430 may be actuated in this manner tens of thousands of times. Various components of the lock out mechanism 430 are therefore selected or configured to withstand such use without wearing out or becoming unreliable. Representatively, to prevent the interface between the hook 432 of the lock out mechanism 430 and the bearing 436 of the lever 314 from becoming worn out over time, the bearing 436 may be a ball bearing that is able to roll along the surface of the hook 432 instead of sliding. For example, if the hook 432 were to hook around a fixed structure instead of balling bearing 436, the two structures would slide along each other until they become disengaged and the trigger releases. This sliding action can wear out these interfacing surfaces over time. The lock out mechanism 430 therefore includes ball bearing 436 which rotates with any triggering action and movement of the hook 432 to ensure that there are no static metal surfaces rubbing and wearing against each other.

In addition, the hook 432 may be configured to reduce wear and improve reliability. For example, the geometry of hook 432 is selected to engage and disengage with the bearing 436 as necessary with minimal wear at the interface. Representatively, referring now to FIG. 9B, FIG. 9B is a magnified view of the hook/bearing interface section shown with dashed lines in FIG. 9A. As can be seen from FIG. 9B, when the lock out mechanism 430 is engaged and waiting to be triggered, the tip 904 of the hook 432 is above (or beyond) the tangent point 906 of the bearing 436. This positions hook 432 so that the bearing 436 is fully nested within the hook 432. When the lockout mechanism 430 begins to be triggered and moves along its rotational path 912, the hook tip 904 moves in a disengagement direction 908 and nears the tangent point 906 of the bearing 436. Once the hook tip 904 reaches that tangent point 906, the bearing 436 will rapidly rotate causing the lock out mechanism 430, which is biased by the spring 902 to disengage the bearing 436, to release the bearing 436. Once released, the bearing 436 moves along rotation path 914 (as a result of the lever 314 rotation about pivot point 422) so that the lever 314 (and first clamp component) can automatically transition to the closed position. The lock out mechanism 430 reengages with the lever 314 when the hook tip 904 is caused to move in the engagement direction 910 and passes the tangent point 906 (e.g. extends beyond the tangent point 906). Accordingly, the geometry of hook 432 may be selected so that it conforms to the bearing 436 outer surface (e.g., curved) and has a depth (D), as measured from tip 904 to the bottom of the hook 916, that allows tip 904 to extend beyond the bearing tangent point 906 when the bearing is fully seated within the hook 432. In addition, as previously discussed, throughout this entire process, the hook 432 is biased by spring 902 into the engaged position to ensure that the trigger does not release until it is purposely triggered. The weight of the spring 902 may therefore also be selected to provide secure engagement without having a noticeable impact on the force required to release the lock out mechanism 430.

In still further aspects, the lock out mechanism 430 may provide audible and/or haptic feedback when it is engaged/disengaged. For example, when the bearing 436 is released from the hook 432, the rolling action allows the bearing to smoothly snap out of the hook and produce an audible and/or haptic feedback notifying the user that the mechanism has been released. In addition, when the lock out mechanism 430 is re-engaged, the bearing 436 may act the same way as it does upon release and the rolling action of the bearing allows the hook to smoothly snap back into place providing the feedback.

In addition, in some aspects, the force needed to trigger the lock out mechanism may be adjustable. As previously discussed, the lock out mechanism has a number of usability advantages within the docking workflow. The force needed to trigger the lock out mechanism and complete docking is critical to the workflow. Too much of a force requirement makes it too difficult for the surgical staff to complete the docking procedure, whereas too little of a force requirement could lead to inadvertent triggering of the lock out mechanism and premature closing of the latch before docking is complete. Being able to adjust this force during assembly allows it to be tuned to the exact level that is desired from a usability perspective.

A representative force adjustment mechanism is shown in FIGS. 9C-9D. Force adjustment mechanism 920 may, in some aspects, be a mechanism or structure that biases lock out mechanism 430 towards disengagement when tightened. For example, force adjustment mechanism 920 may, in some aspects, be a set screw. The set screw may extend through the lock out mechanism 430 and into the interface between the hook/bearing interface when tightened in the direction of arrow 922, as illustrated in FIG. 9C. Representatively, as the lockout adjustment set screw is tightened, it presses against the lockout bearing 436 and shifts the hook 432 such that it has less engagement with the lockout bearing 436 than before it was tightened. In other words, the distance (D1) between the bottom 916 of the hook 432 and the bearing 436 increases. This shortens the distance that the hook 432 has to travel to become disengaged and, in turn, the force required to disengage the lock out mechanism 430 is lowered. The opposite can be achieved by loosening the set screw in the direction of arrow 924, as shown in FIG. 9D. In particular, as shown in FIG. 9D, when the screw is loosened, the distance (D2) between the hook 432 and bearing 436 decreases, resulting in more engagement between the hook 432 and bearing 436. This results in an increase in the force required to disengage the lock out mechanism 430. The position of the adjustment mechanism 430 can be set after assembly of the attachment device and the actuation force can be confirmed before assembling the mechanism into the robotic arm.

In addition, as previously discussed, the interface between the clamping components and the cannula may also play an important role in ensuring a secure attachment between the cannula and the attachment device (and the associated surgical robotic arm). Specific aspects of some representative clamp/cannula alignment or interface structures will now be described in more detail in reference to FIGS. 10A-10C. Although not shown, it should be understood that the attachment device or interface described in reference to FIGS. 10A-10C, although not shown and/or certain parts are omitted, may be substantially the same as the attachment device or interface 212 previously discussed in reference to FIG. 4A-4B.

Figure 10A:
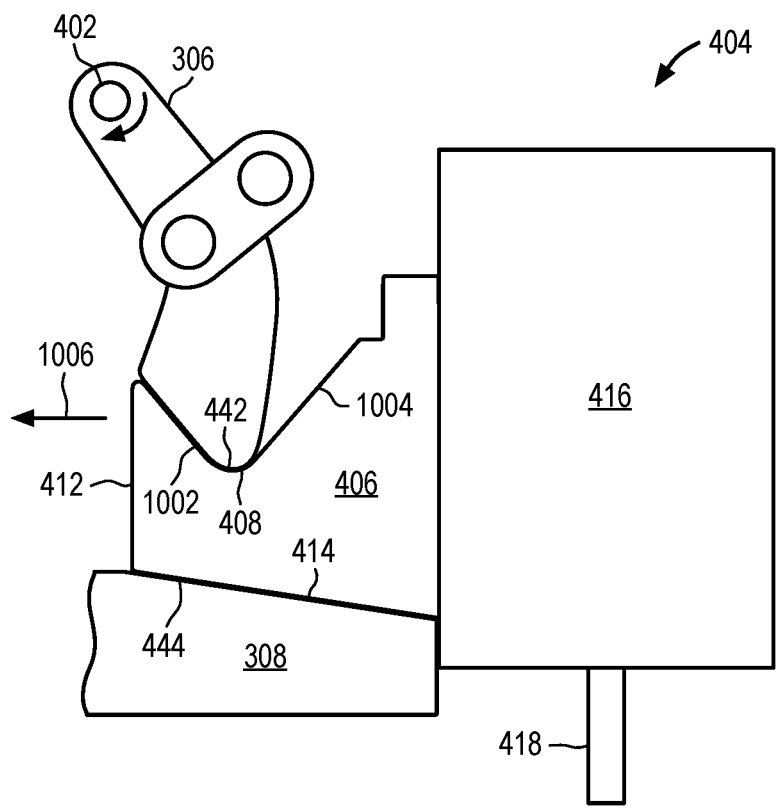
FIG. 10A is a cross-sectional side view of another aspect of the attachment device of FIGS. 4A-4B.

FIG. 10A illustrates a cross-sectional side view of one aspect of an interface or alignment structure of the cannula lug. Representatively, as previously discussed in reference to FIGS. 4A-4B, a top side of the cannula lug 406 may include alignment structure 408. From this view, it can be seen that alignment structure 408 may be considered to have a reverse taper that is formed by sloped surfaces 1002, 1004. The sloped surface 1002, 1004 form a triangular shaped recessed region within the top side of cannula lug 406. First clamp component 306 may, in turn, include a complimentary cannula mating structure 442 which interfaces with structure 408 when the clamp is in the closed position. For example, the mating structure 442 may be a triangular shaped end that is at an angle designed to pull the cannula lug 406 into the attachment device. For example, the reverse taper formed by the structure 408 combined with the angle of clamp structure 442 is designed to pull the cannula lug 406 into the latch in a direction of arrow 1006 when first clamp component 306 is closed to ensure that the cannula is fully seated within the attachment device. The angle of the interface of structures 408, 442 also keeps the cannula 404 securely seated in the attachment device (and against the second clamp component 308) when external forces on the cannula 404 may try to pull it up and out of the attachment device.

Figure 10B:
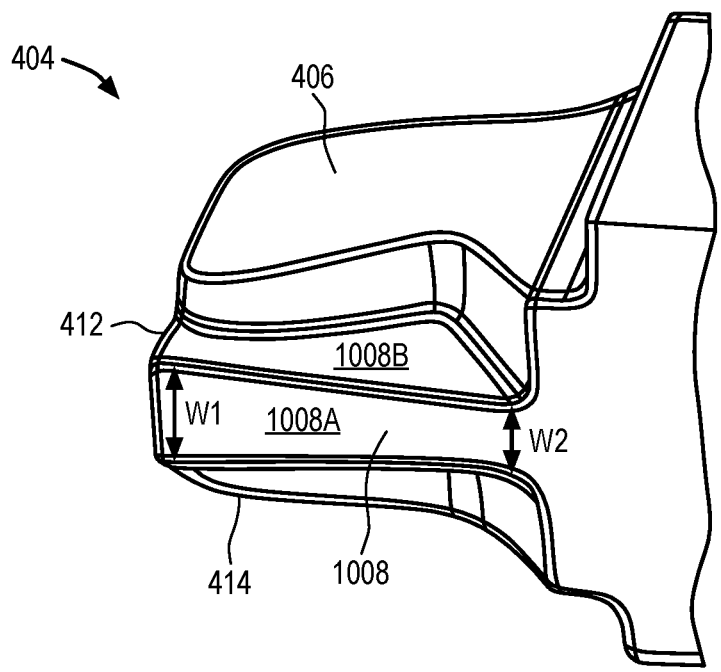
FIG. 10B is a bottom side perspective view of a portion of the attachment device of FIGS. 4A-4B.
Figure 10C:
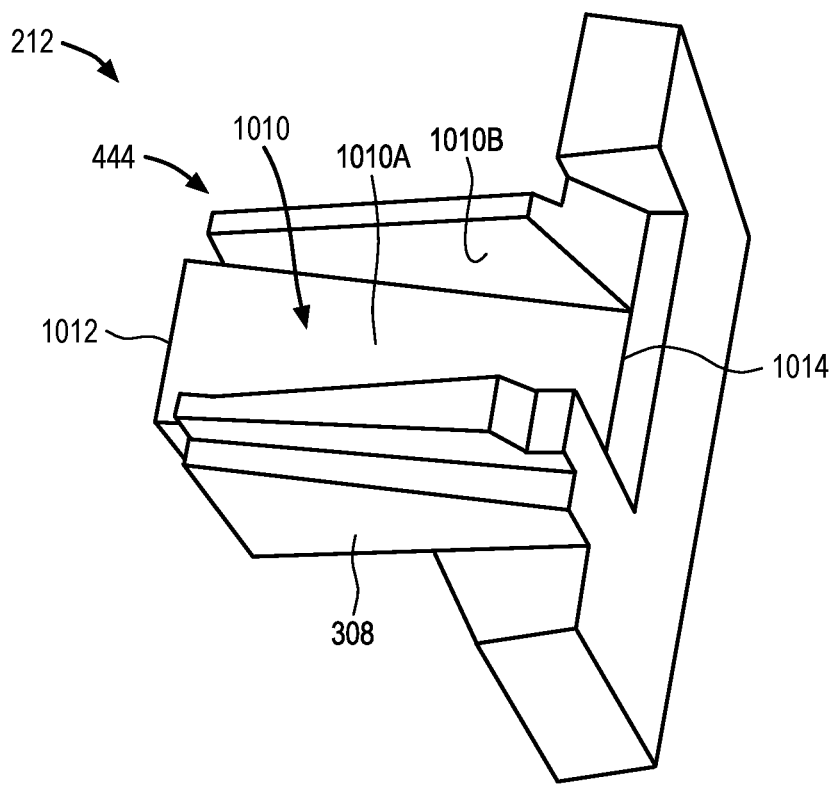
FIG. 10C is a top side perspective view of a portion of the attachment device of FIGS. 4A-4B.

FIG. 10B-10C illustrate perspective views of another aspect of an interface or alignment structure the cannula lug.

Representatively, as previously discussed in reference to FIGS. 4A-4B, a bottom side of the cannula lug 406 may include alignment structure 414 which interfaces with an alignment structure 444 of the second clamp component 308. From this view, it can be seen that alignment structure 414 may include a keel shaped protrusion 1008 formed in the bottom side of the cannula lug 406. The keep shaped protrusion 1008 may be formed by a bottom wall 1008A and side walls 1008B. It should be understood that due to the perspective view, the second side wall 1008B is hidden from view. The bottom wall 1008A may taper inward toward the cannula body 416 such that a width (W1) near end 414 is wider than a width (W2) near body 416. In addition, side walls 1008B may taper inward toward the end 412 so that the structure 414 is sloped as shown in FIG. 10A. The interfacing or complimentary alignment structure 444 on the top side of the second clamp component 308 may, in turn, include a recessed region 1010 having a complimentary configuration to protrusion 1008 so that protrusion 1008 can be inserted within recessed region 1010. Representatively, recessed region 1010 may be formed by a bottom wall 1010A that tapers inward from end 1012 to end 1014, and side walls 1010B that are tapered inward toward the end 1012 so that is complimentary to structure 414. This complimentary configuration of structures 414, 444 helps to guide the insertion of the cannula 404 into the attachment device 212 as well as providing rotational stability. In addition, this configuration helps prevent deflection or twisting of the cannula lug 406 within the attachment device 212 when the cannula 404 is side loaded.

Figure 11A:
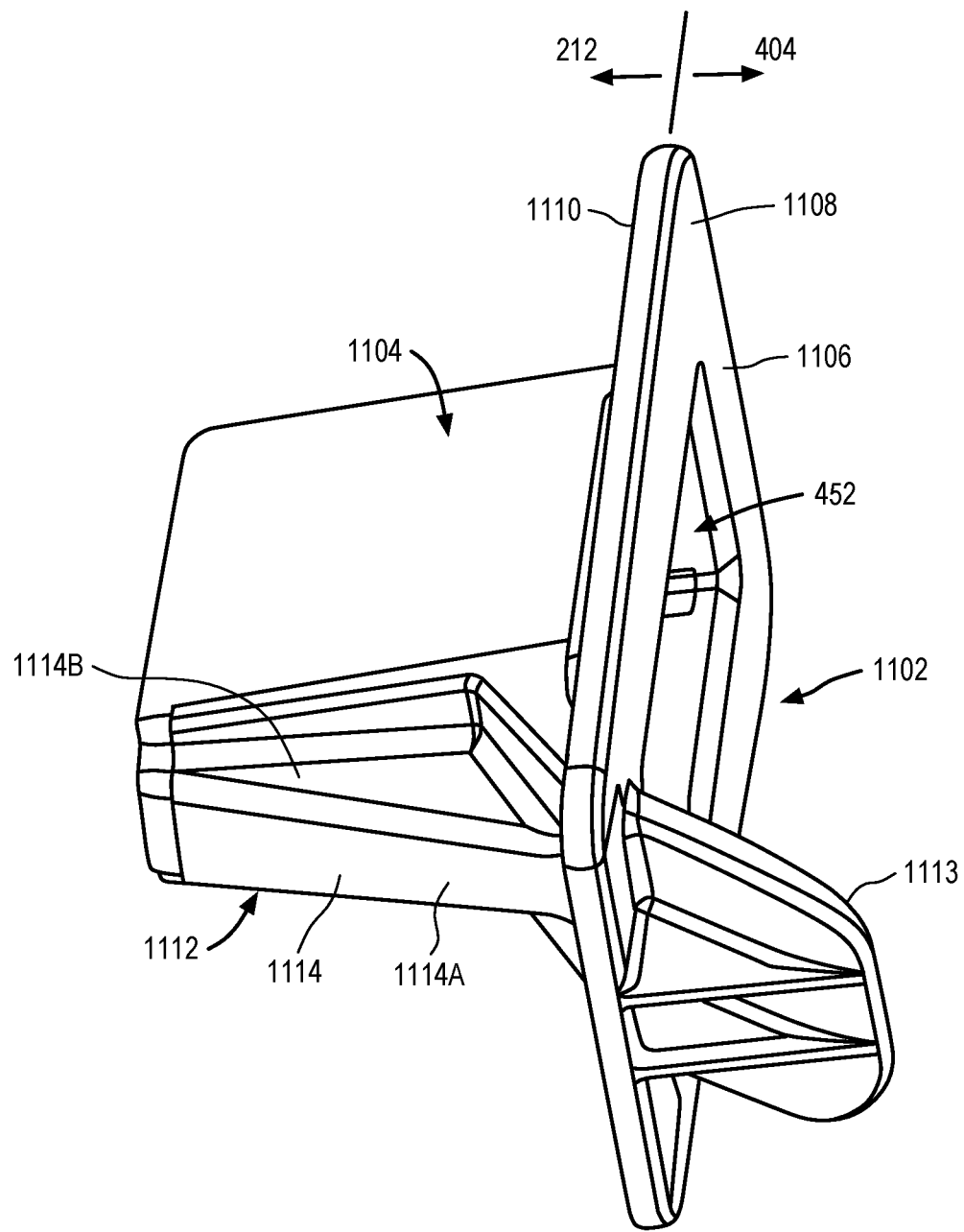
FIG. 11A is a bottom perspective view of a sterile adapter of the attachment device of FIGS. 4A-4B.
Figure 11B:
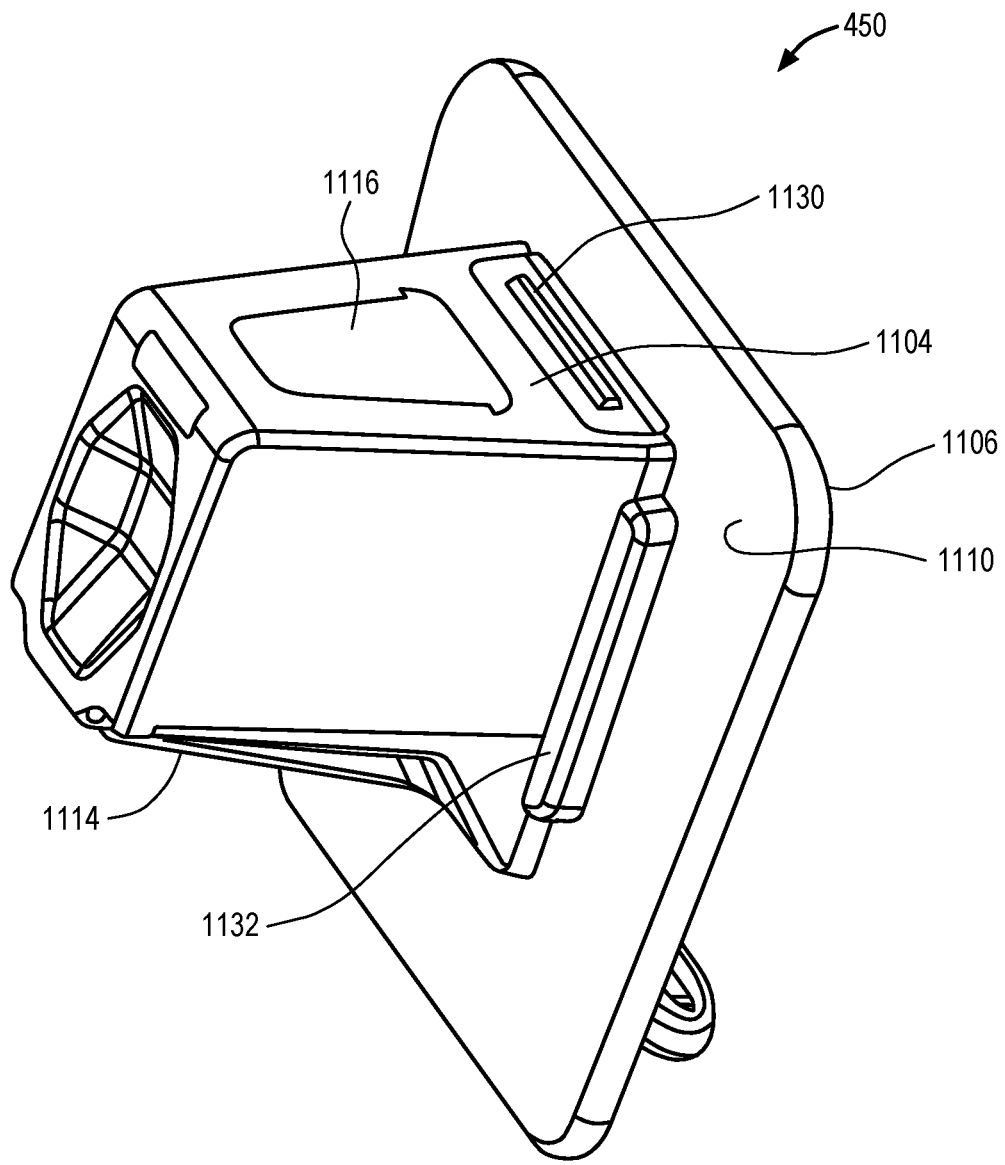
FIG. 11B is a top perspective view of the sterile adapter of FIG. 11A.
Figure 11C:
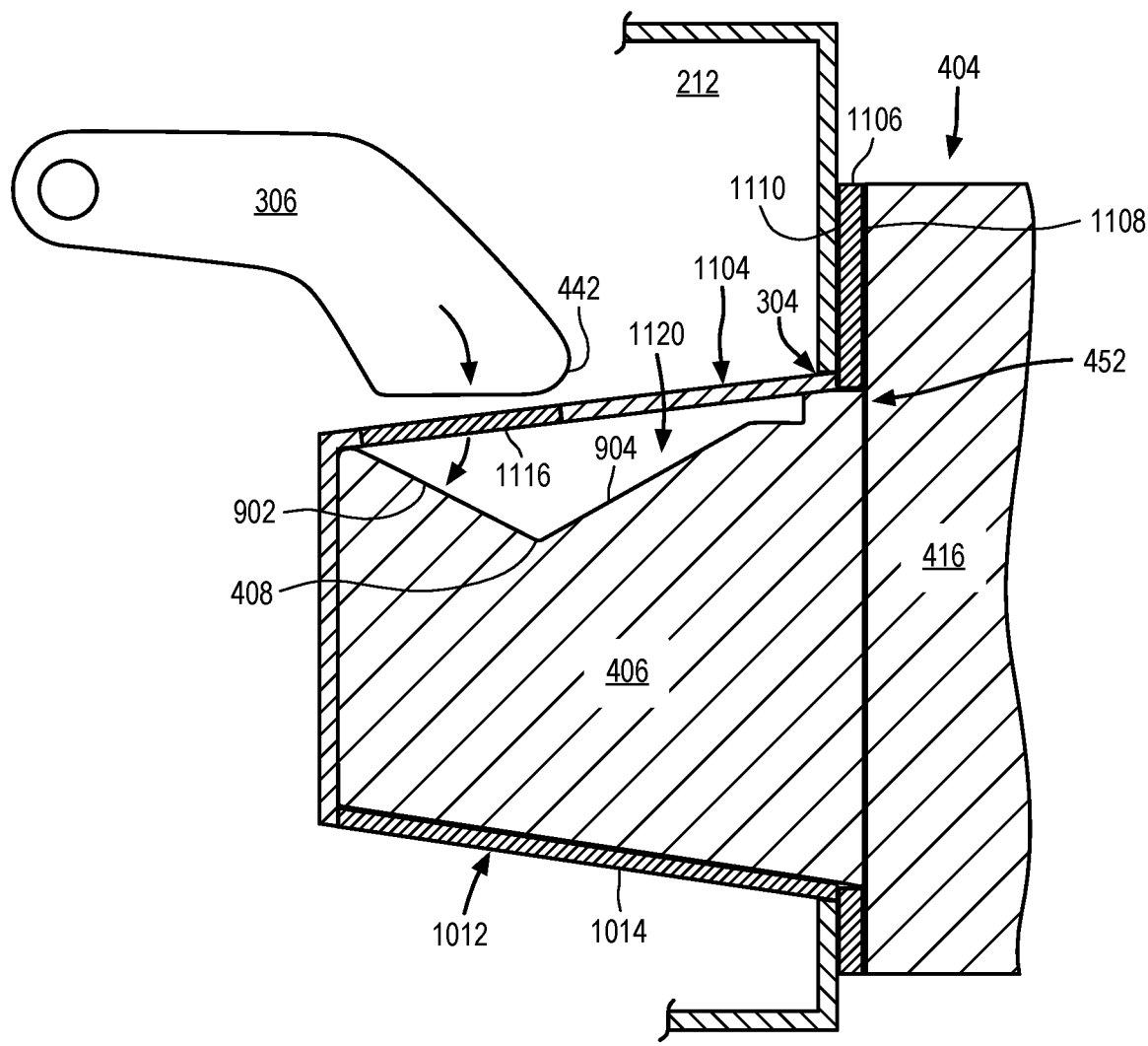
FIG. 11C is a cross-sectional side view of the sterile adapter of FIG. 11A with the attachment device in an open position.
Figure 11D:
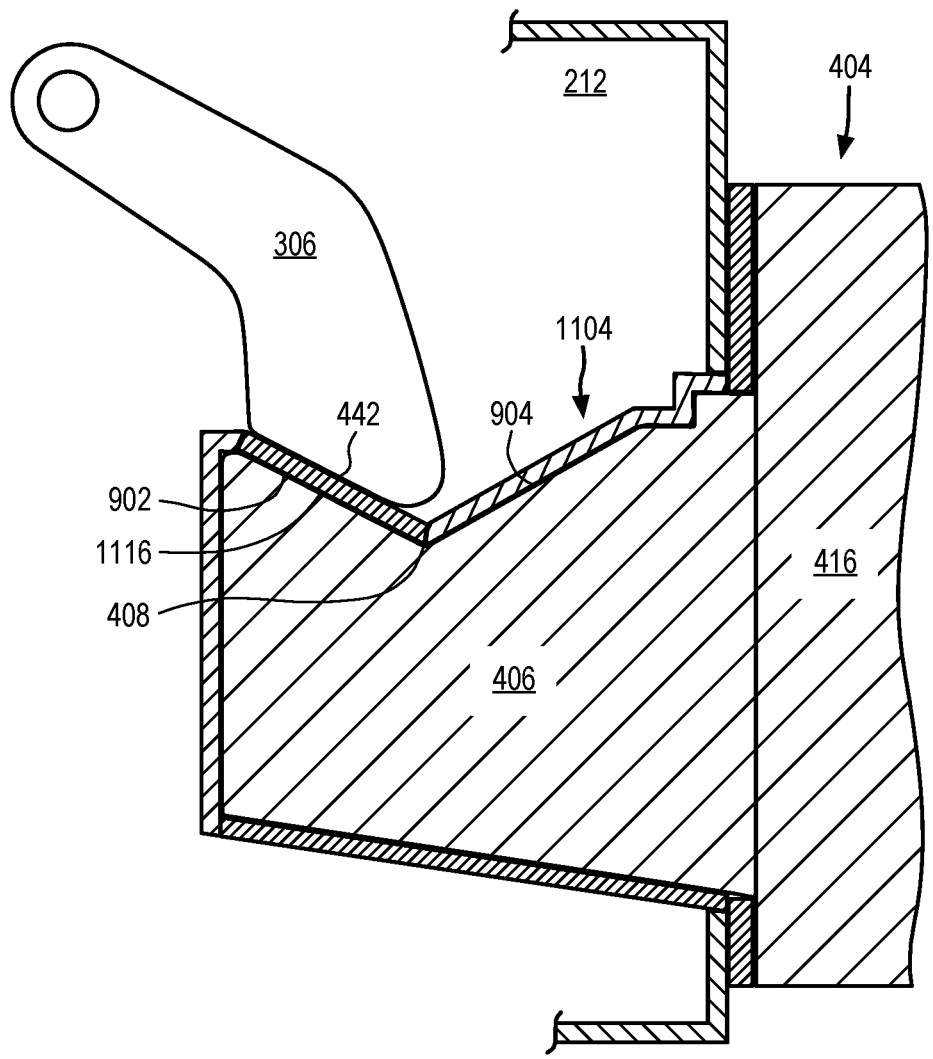
FIG. 11D is a cross-sectional side view of the sterile adapter of FIG. 11A with the attachment device in the closed position.

Returning now to the sterile adapter previously discussed briefly in reference to FIG. 4A-B, the particular details of the sterile adapter will now be described in reference to FIGS. 11A-11D. Representatively, FIGS. 11A-11B illustrate bottom and top perspective views of a sterile adapter, respectively. FIGS. 11C-11D illustrate cross-sectional side view of the sterile adapter illustrated in FIGS. 11A-11B serving as a barrier between the cannula and the attachment device. As previously discussed, the sterile adapter is necessary to maintain the sterile barrier between the robotic arm and the surgical field. The cannula must be rigidly secured through the sterile barrier, however, an entirely rigid or entirely flexible barrier may make it challenging for the attachment device to securely clamp onto the cannula. To solve these challenges, sterile adapter 450 is configured to have hard plastic regions molded together with flexible elastomer regions to form a molded sterile barrier that is both rigid and flexible. The hard plastic/flexible elastomer sterile barrier 450 may be formed by, for example, over molding the rigid plastic pieces to form the rigid portion(s) and then over molding a soft flexible elastomer such as thermoplastic polyurethane (TPU) between the plastic pieces. In this aspect, any rigid plastic pieces that are not directly molded together as a single rigid piece, are connected with the single rigid piece by the flexible elastomer resulting in an integrally formed sterile barrier having inseperable rigid and flexible portions. Representatively, the sterile adapter 450 may include a rigid barrier portion 1102 molded to a flexible barrier portion 1104, which in combination, surround the cannula lug and provide a sterile barrier between the attachment device 212 on one side and the cannula 404 on the other. The rigid barrier portion 1102 may include a cannula interface portion 1106 that defines the opening 452 through which the cannula lug is inserted. The cannula interface portion 1106 may be a substantially flat or plate like member that includes one side that faces the cannula (e.g., cannula side 1108) and an opposite side that faces the attachment device and/or surgical robotic arm (e.g., arm side 1110) when it is inserted into the attachment device opening (e.g., opening 314 of device 212 as shown in FIG. 4A-B). The rigid barrier portion 1102 may also include an alignment interface portion 1112 and an exterior alignment portion 1113 that extend from opposing sides of the cannula interface portion 1106. For example, the exterior alignment portion 1113 may be a lip that extends from the cannula side 1108 of the cannula interface portion 1106 and the alignment interface portion 1112 may extend from the arm side 1110 of rigid portion 1102 and into the device opening (e.g., opening 314 of device 212). The alignment interface portion 1112 may include a mating feature or alignment structure 1114 that is dimensioned to mate with an alignment structures of the cannula lug and second clamp component. Representatively, the alignment structure 1114 may be configured to be positioned between and mate with the alignment structures 414 and 444 of the cannula lug 406 and second clamp component 308, as previously discussed in reference to FIGS. 4A-B and FIGS. 10B-C. In this aspect, the alignment structure 1114 may be on or form the bottom side of the sterile adapter 450 so that it can mate with the structures 414, 444. Alignment structure 1114 may be as rigid and exact as possible so that minimal compression occurs and no clamping force on the cannula lug is lost. For example, similar to alignment structure 444, alignment structure 1114 may be formed by a tapered bottom wall 1114A, and tapered side walls 1114B so that it can receive the alignment structure 414.

In addition, as can be seen from the top perspective view of FIG. 10B, the opposite (or top side) of the sterile adapter 450 includes another rigid alignment structure 1116 that interfaces with the clamping component during a clamping operation. Representatively, the top side rigid alignment structure 1116 may be configured to align with, or otherwise interface with, the alignment structure 442 of the first clamp component 306 and the alignment structure 408 of the cannula lug 406 (see FIGS. 4A-B and FIG. 10A), during a clamping operation. The top side alignment structure 1116 may therefore have any size, shape that allows it to interface with structures 408, 442. For example, top side alignment structure 1116 may have a similar size and shape to structure 408 or structure 442, for example, an elongated shape, a polygon shape or any other suitable shape. The top side alignment structure 1116 made of a same material as the rest of the rigid portion 1102 and be designed to have as little compression as possible since this is the surface that the clamp contacts when clamping against the cannula lug and any compression would result in a reduction in clamping force and retention. The top side alignment structure 1116, however, is entirely surrounded by the flexible barrier portion 1104 to allow for the top side alignment structure 1116 to be able to rotate to the angle of the clamp/lug interface area (e.g., angles between alignment structures 442 of clamp 306 and structure 408 of lug 406) as easily as possible. The modifiable angle of the top side alignment structure 1116 is illustrated in more detail in reference to FIGS. 11C-D. In particular, in FIG. 11C, it can be seen that when the attachment device 212 and first clamp component 306 are in the open configuration, the top side alignment structure 1116 may be substantially aligned with, and form a substantially flat surface with, the remainder of the sterile adapter top side formed by the surrounding flexible barrier portion 1104. When, however, the first clamp component 306 is moved to the closed configuration as shown in FIG. 11D, the first clamp component 306 presses on the top side alignment structure 1116. This, in turn, presses the top side alignment structure 1116 against the surface 1002 of alignment structure 408 of cannula lug 406. In other words, the top side alignment structure 1116 rotates downward and becomes angled relative to the rest of the top side so that it matches the angle of the surface 1002 of the forming the alignment structure 408 of the cannula lug 406. This can occur because the top side alignment structure 1116 is entirely surrounded by the flexible barrier portion 1104. For example, the flexible barrier portion 1104 may act as a hinge allowing the top side alignment structure 1116 to change positions. The rigid/flexible nature of this portion of the sterile adapter 450 is important as the shape of the sterile adapter in the open position is designed to make insertion and removal of the cannula as easy as possible, yet the flexible design ensures that the important mating surfaces of the sterile adapter can conform to the necessary shape for secure attachment (e.g., clamping) with as little force as necessary and as reliably as possible.

Returning now to the flexible barrier portion 1104, as previously discussed the flexible barrier portion is molded to the rigid portion 1102 and is configured to surround the remainder of the cannula lug. In this aspect, the flexible barrier portion 1104 may be molded to, and extend from, the arm side 1110 of the rigid cannula interface portion 1106 and around the opening 452. In this aspect, the flexible barrier portion 1104 may form a cavity 1120 around the opening 452 of the rigid interface portion 1106 that is dimensioned to receive the cannula lug. The cavity 1120 may have a bottom side defined by the rigid alignment portion 1114, a portion of the top side defined by the rigid alignment portion 1116 and the remainder of the cavity is substantially defined by the flexible barrier portion 1104.

Additional aspects of the sterile adapter 450 may include a rigid retention bump 1130 molded to the arm side 1110 of the rigid interface portion 1106 and positioned along the top side of the flexible barrier portion 1104. The retention bump 1130 may, for example, mate with a complimentary mating structure near the opening of attachment device 212 to help to keep the sterile adapter seated in the attachment device 212 during cannula insertion and removal. In addition, the sterile adapter 450 may include one or more rigid mating datums 1132 molded to the arm side of the rigid cannula interface portion 1106 and positioned along a side of the flexible barrier portion 1104. For example, at least one datum(s) 1132 may be positioned along a side of the adapter different from the bump 1130, and/or the top side and bottom side, for example, to a third side that connects the top side and the bottom sides. The rigid mating datum(s) 1132 may be configured in a particular orientation designed to keep the cannula correctly aligned with the tool axis.

Figure 12:
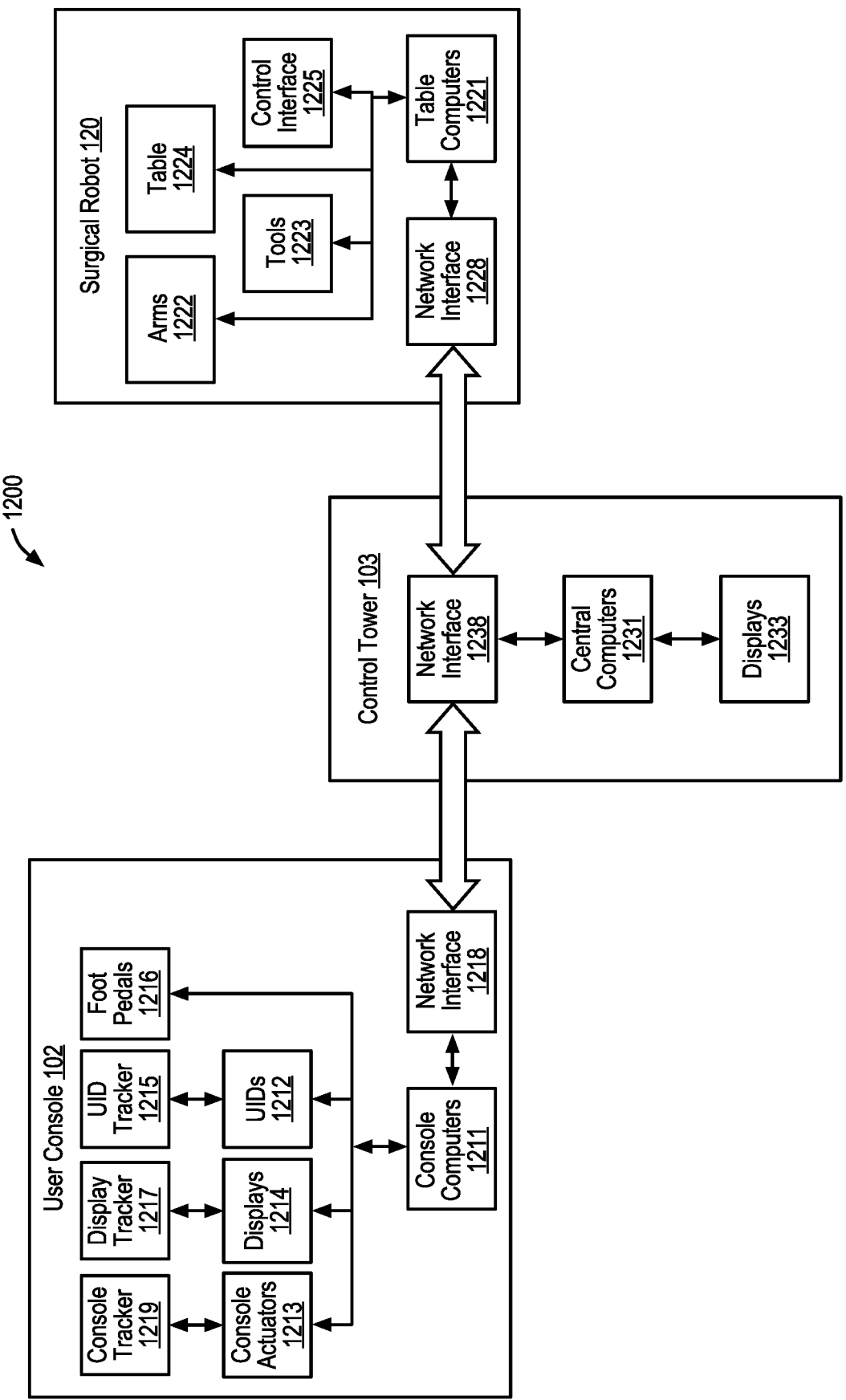
FIG. 12 is a block diagram of a computer portion of a user console for a surgical robotic system including a robotic arm and attachment mechanism, in accordance with an embodiment.

FIG. 12 is a block diagram of a computer portion of a surgical robotic system, which is operable to implement the previously discussed operations, in accordance with an embodiment. The exemplary surgical robotic system 1200 may include a user console 102, a surgical robot 120, and a control tower 103. The surgical robotic system 1200 may include other or additional hardware components; thus, the diagram is provided by way of example and not a limitation to the system architecture.

As described above, the user console 102 may include console computers 1211, one or more UIDs 1212, console actuators 1213, displays 1214, foot pedals 1216, console computers 1211 and a network interface 1218. In addition, user console 102 may include a number of components, for example, a UID tracker(s) 1215, a display tracker(s) 1217 and a console tracker(s) 1219, for detecting various surgical conditions required for operation of the system (e.g., UID orientation, orientation of the surgeon relative to the display, orientation the console seat, etc.). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1213 based on user input or stored configurations by the console computers 1211. The user may perform robot-assisted surgeries by controlling the surgical robot 120 using one or more master UIDs 1212 and foot pedals 1216. Positions and orientations of the UIDs 1212 are continuously tracked by the UID tracker 1215, and status changes are recorded by the console computers 1211 as user input and dispatched to the control tower 103 via the network interface 1218. Real-time surgical video of patient anatomy, instrumentation, and relevant software apps can be presented to the user on the high resolution 3D displays 1214 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 12, the control tower 103 may include central computers 1231 including at least a visualization computer, a control computer, and an auxiliary computer, various displays 1233 including a team display and a nurse display, and a network interface 1218 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an operating table 1224 with a plurality of integrated robotic arms 1222 that can be positioned over the target patient anatomy. A suite of compatible tools 1223 can be attached to or detached from the distal ends of the arms 1222, enabling the surgeon to perform various surgical procedures. The surgical robot 120 may also comprise control interface 1225 for manual or automated control of the arms 1222, table 1224, and tools 1223. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1222 includes four arms mounted on both sides of the operating table 1224, with two arms on each side. For certain surgical procedures, an arm mounted on one side of the table can be positioned on the other side of the table by stretching out and crossing over under the table and arms mounted on the other side, resulting in a total of three arms positioned on the same side of the table 1224. The surgical tool can also comprise table computers 1221 and a network interface 1218, which can place the surgical robot 120 in communication with the control tower 103.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A cannula sterile adapter for attachment of a cannula to a robotic surgical system, the adapter comprising:
   a rigid barrier portion having a cannula interface defining an opening dimensioned to receive a cannula lug, a first cannula interface structure extending from the cannula interface, and a second cannula interface structure, the first cannula interface structure and the second cannula interface structure are dimensioned to interface with alignment structures of a cannula lug; and
   a flexible barrier portion molded to the rigid barrier portion, the flexible barrier portion defining a cavity around the opening of the rigid barrier portion that is dimensioned to receive a cannula lug inserted therein, the cavity having a first side defined by the first cannula interface structure and a second side along which the second cannula interface structure is positioned, and wherein the second cannula interface structure is entirely surrounded by the flexible barrier portion.

2. The adapter of claim 1 wherein the cannula interface comprises a plate having an arm side that faces a robotic surgical arm of the robotic surgical system and a cannula side that faces the cannula lug, and the first cannula interface structure extends from the arm side in a direction of the robotic surgical arm.

3. The adapter of claim 2 wherein the flexible barrier portion is molded to the arm side of the plate and defines at least three sides of the cavity.

4. The adapter of claim 1 wherein the first cannula interface structure comprises a keel shaped structure dimensioned to interface with a complimentary recessed region of the cannula lug.

5. The adapter of claim 1 wherein the second cannula interface structure comprises a plate molded to the second side.

6. The adapter of claim 5 wherein an angle of the plate is modifiable to an angle of the alignment structures of the cannula lug.

7. The adapter of claim 1 further comprising a retention bump coupled to the second side of the flexible barrier portion, the retention bump dimensioned to retain the cannula sterile adapter within a clamping assembly during insertion and removal of the cannula lug within the clamping assembly.

8. The adapter of claim 1 further comprising a mating datum coupled to a third side of the flexible barrier portion and configured to maintain an alignment between the cannula lug inserted therein and an axis of an associated tool.

9. The adapter of claim 1 wherein the rigid barrier portion is formed by a plastic material.

10. The adapter of claim 1 wherein the flexible barrier portion is formed by a flexible elastomeric material that is overmolded to the rigid barrier portion.

11. The adapter of claim 1 wherein the flexible barrier portion comprises thermoplastic polyurethane.

12. A cannula sterile adapter for attachment of a cannula to a robotic surgical system, the adapter comprising:
    a rigid barrier portion having a cannula interface defining an opening dimensioned to receive a cannula lug, a first cannula interface structure extending from the cannula interface, and a second cannula interface structure that is movable relative to the cannula interface, the first cannula interface structure and the second cannula interface structure are dimensioned to interface with alignment structures of a cannula lug; and
    a flexible barrier portion molded to the rigid barrier portion, the flexible barrier portion defining a cavity around the opening of the rigid barrier portion that is dimensioned to receive a cannula lug inserted therein, the cavity having a first side defined by the first cannula interface structure and a second side along which the second cannula interface structure is positioned.

13. The adapter of claim 12 wherein the cannula interface comprises a plate having an arm side that faces a robotic surgical arm of the robotic surgical system and a cannula side that faces the cannula lug, and the first cannula interface structure extends from the arm side in a direction of the robotic surgical arm.

14. The adapter of claim 13 wherein the flexible barrier portion is molded to the arm side of the plate and defines at least three sides of the cavity.

15. The adapter of claim 12 wherein the first cannula interface structure comprises a keel shaped structure dimensioned to interface with a complimentary recessed region of the cannula lug.

16. The adapter of claim 12 wherein the second cannula interface structure comprises a plate molded to the second side of the flexible barrier portion.

17. The adapter of claim 16 wherein an angle of the plate is modifiable to an angle of the alignment structures of the cannula lug.

18. The adapter of claim 16 wherein the plate is entirely surrounded by the flexible barrier portion.

19. The adapter of claim 12 further comprising a retention bump coupled to the second side of the flexible barrier portion, the retention bump dimensioned to retain the cannula sterile adapter within a clamping assembly during insertion and removal of the cannula lug within the clamping assembly.

20. The adapter of claim 12 wherein the rigid barrier portion is formed by a plastic material and the flexible barrier portion is formed by a flexible elastomeric material that is overmolded to the plastic material.

* * * * *